US012347564B2

(12) United States Patent
Ahmed et al.

(10) Patent No.: US 12,347,564 B2
(45) Date of Patent: Jul. 1, 2025

(54) TIMELY DETECTION AND RESPONSE TO CONTEXT-SPECIFIC HEALTH EVENTS

(71) Applicant: SAMSUNG ELECTRONICS CO., LTD., Gyeonggi-Do (KR)

(72) Inventors: Tousif Ahmed, San Jose, CA (US); Md Mahbubur Rahman, San Jose, CA (US); Sean Bornheimer, San Francisco, CA (US); Nathan Robert Folkman, San Francisco, CA (US); Anh Minh Dinh, San Francisco, CA (US); Ebrahim Nematihosseinabadi, San Jose, CA (US); Jilong Kuang, San Jose, CA (US); Jun Gao, Menlo Park, CA (US)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 483 days.

(21) Appl. No.: 17/728,741

(22) Filed: Apr. 25, 2022

(65) Prior Publication Data

US 2023/0343458 A1    Oct. 26, 2023

(51) Int. Cl.
*G16H 50/30*    (2018.01)
*A61B 5/00*    (2006.01)
(Continued)

(52) U.S. Cl.
CPC .......... *G16H 50/30* (2018.01); *A61B 5/0022* (2013.01); *A61B 5/7282* (2013.01); *G16H 10/60* (2018.01); *G16H 80/00* (2018.01); *H04W 4/023* (2013.01)

(58) Field of Classification Search
None
See application file for complete search history.

(56) References Cited

U.S. PATENT DOCUMENTS 9,161,198 B2   10/2015   Dalton et al.
9,892,612 B2    2/2018   Smits et al.
(Continued)

FOREIGN PATENT DOCUMENTS

EP          3234826 B1      9/2019
KR     20190059437 A        5/2019
(Continued)

OTHER PUBLICATIONS

WIPO Appln. PCT/KR2023/003236 International Search Report, Jun. 27, 2023, 3 pg.

(Continued)

*Primary Examiner* — Thomas S McCormack
(74) *Attorney, Agent, or Firm* — Kevin T. Cuenot

(57) ABSTRACT

Detecting an adverse health event and responding to an emergency event can include updating a current context profile of a user based on signals generated by one or more sensors of a device, the signals generated in response to one or more physically measurable phenomena associated with the user. A context-aware baseline profile having a same context as the current context profile can be selected, the context-aware baseline profile selected from a plurality of context-aware baseline profiles having different contexts. Features of the current context profile can be compared with corresponding features of the context-aware baseline profile of the user having the same context as the current context profile. A remedial action can be initiated in response to recognizing, based on the comparing, an occurrence of a possible adverse health event affecting the user.

18 Claims, 14 Drawing Sheets

(51) Int. Cl.
*G16H 10/60* (2018.01)
*G16H 80/00* (2018.01)
*H04W 4/02* (2018.01)

(56) References Cited

U.S. PATENT DOCUMENTS

| | | | |
|---|---|---|---|
| 10,842,390 | B2 | 11/2020 | Cronin et al. |
| 10,846,599 | B2 | 11/2020 | Shams et al. |
| 2013/0135097 | A1 | 5/2013 | Doezema |
| 2014/0143064 | A1* | 5/2014 | Tran ............. G16H 40/67 705/14.66 |
| 2014/0247154 | A1 | 9/2014 | Proud |
| 2015/0125832 | A1 | 5/2015 | Tran |
| 2016/0050037 | A1 | 2/2016 | Webb |
| 2016/0086500 | A1* | 3/2016 | Kaleal, III ............. A61B 5/43 434/257 |
| 2017/0071506 | A1 | 3/2017 | Dwarika |
| 2017/0337339 | A1 | 11/2017 | Cronin et al. |
| 2021/0065912 | A1 | 3/2021 | De Vries et al. |
| 2021/0261135 | A1 | 8/2021 | O'Flaherty |

FOREIGN PATENT DOCUMENTS

| | | | |
|---|---|---|---|
| WO | 2014172312 | A2 | 10/2014 |
| WO | 2021050950 | A1 | 3/2021 |

OTHER PUBLICATIONS

WIPO Appln. PCT/KR2023/003236 Written Opinion, Jun. 27, 2023, 4 pg.

Mishra, T, et al., "Pre-symptomatic detection of COVID-19 from smartwatch data," Nature Biomedical Engineering, Dec. 2020, vol. 4, No. 12, pp. 1208-1220.

Alavi, A. et al., "Real-time alerting system for COVID-19 and other stress events using wearable data," Nature Medicine, Jan. 2022, vol. 28, No. 1, pp. 175-184.

Chan, J. et al., "Contactless cardiac arrest detection using smart devices," NPJ Digital Medicine, Jun. 2019, vol. 2, No. 1, pp. 1-8.

Kumar, A. et al., "Estimating Respiratory Rate From Breath Audio Obtained Through Wearable Microphones," In2021 43rd Annual International Conference of the IEEE Engineering in Medicine & Biology Society (EMBC), Nov. 1, 202, pp. 7310-7315, IEEE.

Hassan, T. et al., "Automatic detection of pain from facial expressions: a survey," IEEE Transactions on Pattern Analysis and Machine Intelligence, Dec. 9, 2019, vol. 43, No. 6, pp. 1815-1831.

Spille, C. et al., "Predicting speech intelligibility with deep neural networks," Computer Speech & Language, Mar. 1, 2018, vol. 48, pp. 51-66, (Abstract).

Arends, J.B., "Movement-based seizure detection," Epilepsia, Jun. 2018, vol. 59, pp. 30-35.

He, Y, et al., "Physical activity recognition utilizing the built-in kinematic sensors of a smartphone," International Journal of Distributed Sensor Networks, Apr. 10, 2013, vol. 9, No. 4, pp. 481580.

Beniczky, S. et al., "Detection of generalized tonic-clonic seizures by a wireless wrist accelerometer: a prospective, multicenter study," Epilepsia, Apr. 2013, vol. 54, No. 4, pp. e58-e61.

Ahmed, E., "Facebook (now Meta) wants in on healthcare, but it's too late," [online] eMarketer, Insider Intelligence Inc. © 2022, Oct. 29, 2021, retrieved from the Internet: <https://www.emarketer.com/content/facebook-now-meta-wants-on-healthcare-it-s-too-late>, 7 pg.

Ep23796608, Extended Eureopean Search Report, Feb. 19, 2025, 8 pg.

* cited by examiner

← 700

| Context | Sensor Type | Recording Frequency |
|---|---|---|
| Emergency | Motion Sensors, Multimedia Sensors | Continuous Recording |
| Continuous Sensing | Motion Sensors | Continuous Recording |
| | Multimedia Sensors | Intermittently |

TIMELY DETECTION AND RESPONSE TO CONTEXT-SPECIFIC HEALTH EVENTS

TECHNICAL FIELD

This disclosure relates to detecting and responding to abnormal health events, and more particularly, to determining in real-time the seriousness of an adverse health event and providing a response thereto.

BACKGROUND

An adverse health event can be characterized by a sudden change in the physiological condition or state of an individual. The change can result, for example, from a cardiovascular event such as cardiac arrest, from a neurological event such as a stroke or seizure, from an accident such as a fall, from a respiratory event, or from various other health-related events. Such events, regardless of the underlying cause, often involve medical emergencies in which the time for responding can be critical to an individual's survivability and prospects of recovery following the sudden occurrence of such an event. Unfortunately, in many situations, the individual experiencing a medical emergency may be alone or unable to communicate effectively. In such situations, the individual may be unable to inform anyone of the nature of the adverse health event or request emergency assistance.

SUMMARY

In an example implementation, an automated health event and detection method can include updating a current context profile of a user based on signals generated by one or more sensors of a wearable device, the signals generated in response to one or more physically measurable phenomena associated with the user. The method can include selecting a context-aware baseline profile having a same context as the current context profile, the context-aware baseline profile selected from a plurality of context-aware baseline profiles having different contexts. The method can include comparing features of the current context profile with corresponding features of the context-aware baseline profile of the user having the same context as the current context profile. The method can include initiating a remedial action in response to recognizing, based on the comparing, an occurrence of a possible adverse health event affecting the user.

In another example implementation, a system can include one or more processors configured to initiate operations. The operations can include updating a current context profile of a user based on signals generated by one or more sensors, the signals generated in response to one or more physically measurable phenomena associated with the user. The operations can include selecting a context-aware baseline profile having a same context as the current context profile, the context-aware baseline profile selected from a plurality of context-aware baseline profiles having different contexts. The operations can include comparing features of the current context profile with corresponding features of the context-aware baseline profile of the user having the same context as the current context profile. The operations can include initiating a remedial action in response to recognizing, based on the comparing, an occurrence of a possible adverse health event affecting the user.

In yet another example implementation, a computer program product includes one or more computer readable storage media, and program instructions collectively stored on the one or more computer readable storage media. The program instructions are executable by computer hardware to initiate operations. The operations can include updating a current context profile of a user based on signals generated by one or more sensors, the signals generated in response to one or more physically measurable phenomena associated with the user. The operations can include selecting a context-aware baseline profile having a same context as the current context profile, the context-aware baseline profile selected from a plurality of context-aware baseline profiles having different contexts. The operations can include comparing features of the current context profile with corresponding features of the context-aware baseline profile of the user having the same context as the current context profile. The operations can include initiating a remedial action in response to recognizing, based on the comparing, an occurrence of a possible adverse health event affecting the user.

This Summary section is provided merely to introduce certain concepts and not to identify any key or essential features of the claimed individual matter. Other features of the inventive arrangements will be apparent from the accompanying drawings and from the following detailed description.

BRIEF DESCRIPTION OF THE DRAWINGS

The inventive arrangements are illustrated by way of example in the accompanying drawings. The drawings, however, should not be construed to be limiting of the inventive arrangements to only the particular implementations shown. Various aspects and advantages will become apparent upon review of the following detailed description and upon reference to the drawings.

FIG. 7 illustrates an example rule set implemented by a context-aware privacy manager of the system of FIG. 1.

DETAILED DESCRIPTION

Figure 1:
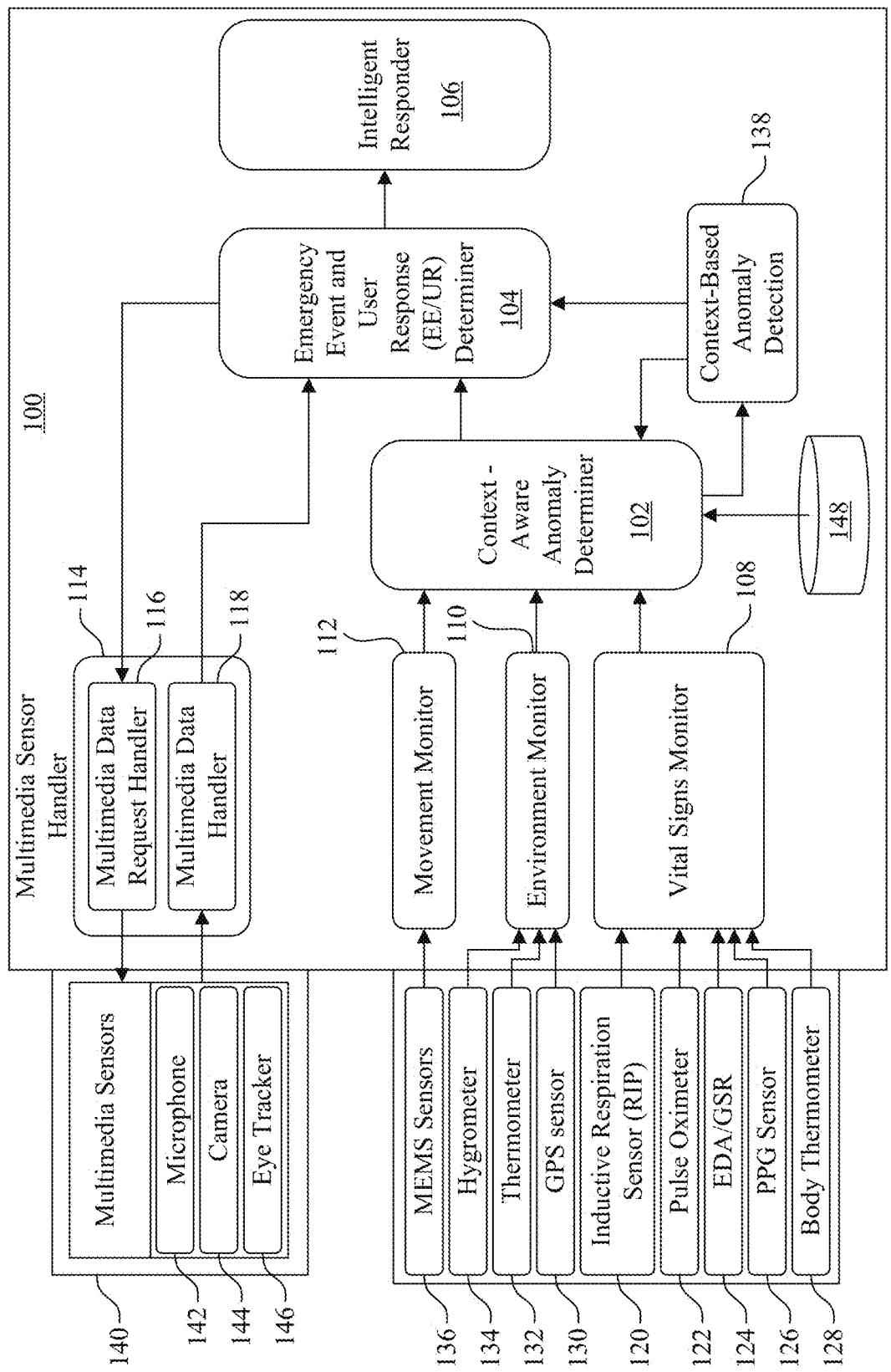
FIG. 1 illustrates an example adverse health event detection and emergency response system.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

This disclosure relates to detecting and responding to abnormal health events, and more particularly, to determining the seriousness of an adverse health event and providing a response thereto. In certain aspects, the adverse health event and/or determination of the seriousness thereof may be performed in real-time. As already noted, often an adverse health event occurs when the person experiencing the event is alone. The adverse health event, moreover, may render the person unable to effectively communicate and thus unable to explain the nature of the event or even call for help. This can be particularly problematic because many elderly individuals who are typically more likely than others to experience an adverse health event often live alone.

A possible solution is a device capable of detecting indications of an adverse health event and responding automatically by initiating a call for emergency assistance. A device having one or more sensors that generate signals for measuring the device user's vital signs, such as heart rate, respiration rate, and other physiological measurements, can detect a possible adverse health event. Given the unpredictable timing of such events, the device would need to be ever-present with the user—either worn by the user or carried close enough to the user to detect when the user experiences an adverse event. Thus, ideally, the device is portable.

To be a reliable indicator of an adverse health event, the device must be able to distinguish between vital sign values that are normal and those that are abnormal and thus indicative of an adverse health event. One challenge is the fact that what is an abnormal measurement in one context may be normal in another. An individual's vital signs are highly dependent on context, that is, the individual's activity, environment, and other contextual facets that can affect the individual's physiology at a given instant of time. For example, if the individual's heart rate is over 120 bpm while resting, the elevated heart rate may well indicate cardiac distress or other emergency health event. If the same individual's heart rate is over 120 bpm while engaging in strenuous activity (e.g., exercising), that same heart rate may be normal. The challenge is compounded by the fact that a vital sign measurement that is abnormal for one individual may be normal for another. Differences in individuals' physiology may stem from differences in age, sex, underlying health condition, or similar contextual parameters having little or nothing to do with an adverse health event.

In accordance with the inventive arrangements described herein, example methods, systems, and computer program products are provided that are capable of automatically determining in real-time a likely adverse health event of an individual and initiating a remedial action in response thereto. An aspect of the inventive arrangements disclosed is determining a likely adverse health event with enhanced accuracy based on comparing a user's current, context-aware health profile (e.g., matrix) with a user-specific, context-aware baseline profile having the same context. As defined herein, a "context" is a set of values of a plurality of contextual parameters that affect the user's physiological condition or state. Relatedly, a "contextual parameter," as defined herein is a measurable or observable variable corresponding to a physical factor or phenomenon that can affect a user's physiology. Such factors can include, for example, a current activity in which the user is engaged, the user's current surroundings, the user's underlying health condition, and other factors, including demographic factors such as the user's sex and age. For example, context can include a locational context (e.g., indoors or outdoors), an activity context (e.g., sitting, sleeping, exercising, climbing stairs) and an environmental context (e.g., ambient temperature, humidity, altitude).

Accordingly, this aspect of the inventive arrangements allows for more accurate detection of an adverse health event by considering the user's current vital signals in the specific context in which the vital signs are measured by one or more sensors. The user's current, context-aware vital signs are compared to baseline measurements that reflect the same context as the user's current vital signs, thus enhancing detection accuracy.

The inventive arrangements disclosed, in certain arrangements, are implemented in a wearable device, such as a pair of earbuds, smartwatch, smart glasses (including a virtual-, an augmented-, or a mixed-reality head-mounted display (HMD) device), chest band, or similar such device. In other arrangements, the inventive arrangements are implemented in multiple devices operatively coupled with one another. One device, such as a wearable device having sensing capabilities, can operatively couple with another device, such as a smartphone, tablet, or laptop, having greater processing capabilities as well as additional sensing capability.

The device with which the inventive arrangements are implemented and/or a companion device with which the device is operatively coupled can include multiple sensors. The sensors can include physiological sensors, geolocation and environmental sensors, movement sensors, as well as multimedia sensors (e.g., microphone, video camera, eye movement tracker). The physiological sensors can generate signals from which various physiological data are derived, such as the heart rate, respiration rate, and blood oxygen saturation level of a user.

One aspect of the inventive arrangements disclosed herein is the implementation of one or more machine learning models that can classify movements and physical conditions of the user based on data derived from motion sensor-generated signals and signals captured by multimedia sensors. For example, machine learning classification of signals generated by an inertial measurement unit (IMU) or other microelectromechanical (MEM) motion sensor can detect a user's fall. Machine learning classification of signal(s) generated by an eye tracking unit, for example, can detect a user's unconsciousness.

One of the advantages of the contextual information provided by such sensors and machine learning models is an enhanced capability to accurately determine the nature of an adverse health event. As described herein, such information can be used as part of the automated response provided by the disclosed arrangements that enables a health professional or other assistor to more accurately assess and respond correctly to the condition of a user who experiences an adverse health event.

Another of the advantages is mitigation of false positives without adding to processing overhead. Continuous monitoring can be performed using multiple lightweight sensors to monitor the user's vital signs, but such sensors tend to be susceptible to motion artifacts. If only lightweight sensors are used in detecting an adverse health event, there is a greater likelihood of a false positive. Using multimedia sensors can provide more accurate results. Given the overhead incurred with the use of multimedia sensors, however, may make continuous monitoring with multimedia sensors infeasible for use in a portable device (e.g., earbuds, smartwatch, smart glasses).

The inventive arrangements overcome the dilemma by using multimedia sensors to enhance detection accuracy but do so only in response to an initial determination that there is a high likelihood of an emergency due to an adverse health event. If based on continuous monitoring there is less certainty of the seriousness of a possible adverse health event, then the inventive arrangements initiate continued, albeit enhanced, monitoring of the user's condition. Thus, another aspect of the inventive arrangements is the selective use of multimedia sensors to enhance detection accuracy while avoiding excessive drain of the resources of the device and sensors used for detecting and responding to adverse health events.

Further aspects of the inventive arrangements are described below in greater detail with reference to the figures. For purposes of simplicity and clarity of illustration, elements shown in the figures are not necessarily drawn to scale. For example, the dimensions of some of the elements may be exaggerated relative to other elements for clarity. Further, where considered appropriate, reference numbers are repeated among the figures to indicate corresponding, analogous, or like features.

Referring initially to FIG. 1, an example adverse health event detection and response system (system) 100 is depicted. Illustratively, system 100 includes context-aware anomaly determiner 102, emergency event and user response (EE/UR) determiner 104, intelligent responder 106, vital signs monitor 108, environment monitor 110, movement monitor 112, and multimedia sensor handler 114. Multimedia sensor handler 114 illustratively includes both multimedia data request handler 116 and multimedia data handler 118.

Figure 13:
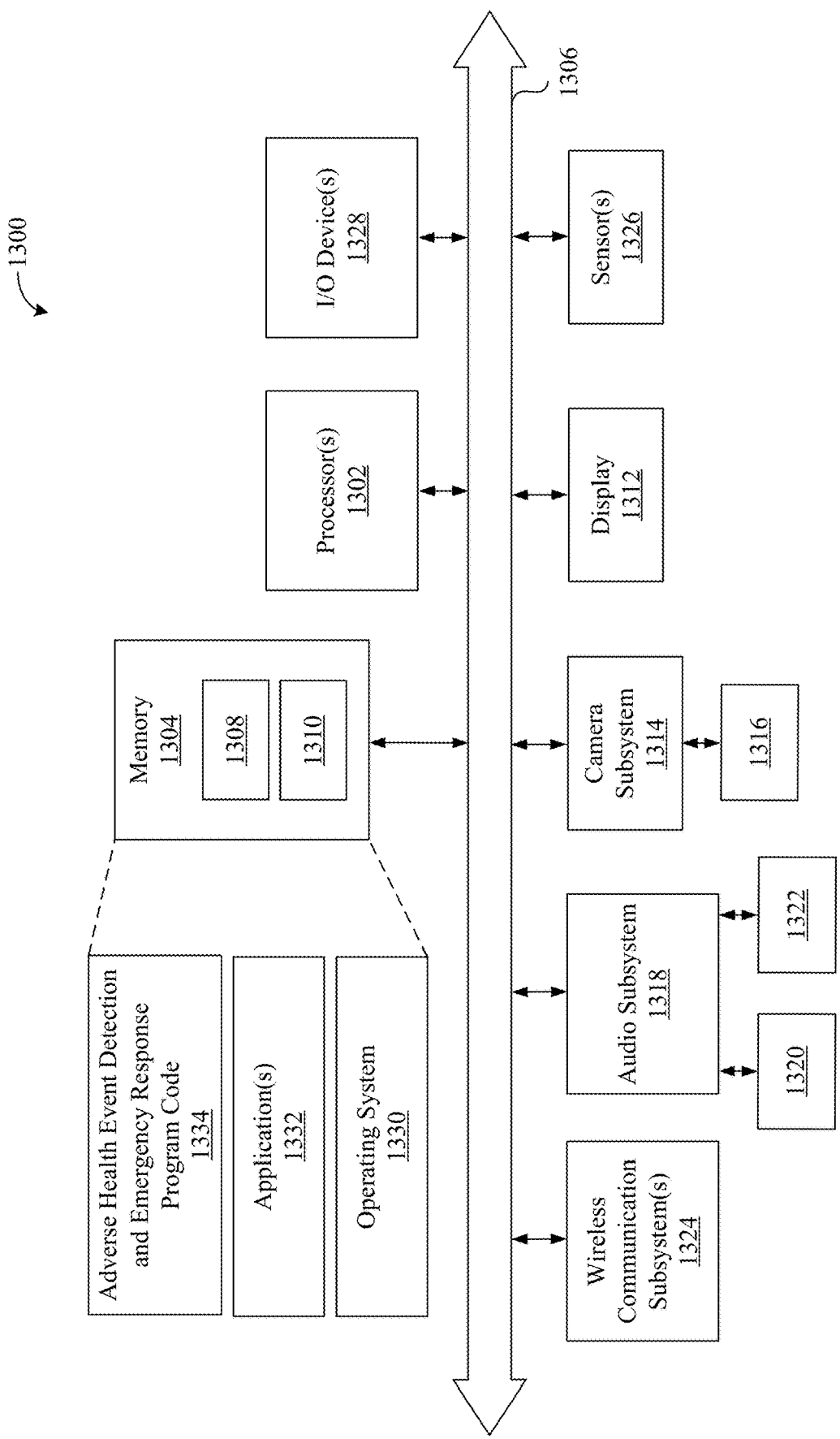
FIG. 13 illustrates an example electronic device used in implementing the system of FIG. 1.

System 100, in various arrangements, can be implemented in hardware (e.g., dedicated hardwired circuitry), software (e.g., program code executed by one or more processors), or a combination thereof. For example, system 100 in certain embodiments is implemented in a device such as device 1300 (FIG. 13). Accordingly, in certain arrangements, system 100 comprises program code that is electronically stored in a memory, such as memory 1304, and executes on one or more processors, such as processor(s) 1302 of device 1300 (FIG. 13). The device can be a wearable device such as a health-monitoring device (e.g., chest band) worn by a user or a multifunctional device such as a smartwatch, smart glasses, ear buds, or other device, including a virtual reality, augmented reality, or mixed reality HMD device.

System 100 performs various functions based on context-aware data generated in real-time by the processing of various signals as described below. The signals may be generated by a variety of different types of sensors communicatively coupled to vital signs monitor 108, environment monitor 110, movement monitor 112, and multimedia sensor handler 114. Accordingly, in various arrangements, different elements of system 100 can be implemented in separate devices that operatively couple to one another. For example, signals captured by sensors of a wearable device (e.g., earbuds, smart glasses) may undergo signal processing by a companion device (e.g., smartphone, smartwatch, cloud-based server) that wirelessly operatively couples with the wearable device and has heavy-weight processing capabilities.

Sensor-generated signals, processed by system 100, are used by the system to construct a current context profile of a user. The current context profile provides a real-time indication of the user's physiological condition or state given a corresponding set of contextual factors, including the user's current activity and environment. System 100 compares the current context profile to a baseline profile corresponding to the same context to identify any abnormalities in the user's physiology and to respond accordingly.

Vital signs monitor 108 processes signals generated by various sensors operatively coupled with system 100. The sensors illustratively include inductive respiration sensor (RIP) 120, pulse oximeter 122, electrodermal and galvanic skin response (EDA/GSR) sensors 124, photoplethysmography (PPG) sensor 126, and thermometer 128. Various combinations of these and/or other sensors in different arrangements can operatively couple with system 100. Data derived from the sensor-generated signals and processed by vital signs monitor 108 can include, for example, the user's respiration rate, heart rate, blood oxygen saturation ($SpO_2$), and core body temperature. In other arrangements, the same and/or other data can be processed by vital signs monitor 108 depending on the various sensors operatively coupled with system 100.

The user's physiological state or condition is one dimension of the overall context. The context also can include the user's activity, as well as the user's location and environment. Activity, location, and environment can each affect the user's current physiological condition or state. For example, the user's respiration and heart rates are expected to be higher if the user is engaged in strenuous activity (e.g., exercising) as opposed to being sedentary. Similarly, the user's core body temperature is likely to be affected by whether the user is indoors or outdoors on a hot, humid day as opposed to a cold, snowy day. The accuracy of system 100 in identifying physiological indicia indicating an abnormality or adverse health condition is enhanced by comparing the user's current context profile to a context-aware baseline profile corresponding to the same context.

Environment monitor 110 and movement monitor 112, like vital signs monitor 108, determine contextual parameters through the processing of signals generated by various other sensors operatively coupled with system 100. Geolocation and environmental data processed by environment monitor 110 can be derived from sensors that illustratively include global positioning system (GPS) sensor 130, thermometer 132, and hygrometer 134. In other arrangements, combinations of these and/or different sensors can operatively couple with system 100. Based on data derived from the various sensor-generated signals, environment monitor 110 can determine various contextual parameters that affect the physiological condition of the user. The contextual parameters include, for example, geolocation data for determining whether the user is indoors or outdoors, the ambient temperature, air pressure, barometric pressure, and humidity. In other arrangements, the same and/or other data can be processed by environment monitor 110 depending on the various sensors operatively coupled with system 100.

Movement monitor 112 processes user movements detected by movement-detecting sensors. Illustratively, the movement-detecting sensors include one or more microelectromechanical systems (MEMS) sensors 136. MEMS sensor(s) 136 can include, in different arrangements, accelerometers, magnetometers, and the like. In certain arrangements, MEMS sensor(s) 136 include an inertial measurement unit (IMU) that combines a MEMS accelerometer and a MEMS gyroscope. Implemented in an IMU, in some arrangements, MEMS sensor(s) 136 can be embedded in a wearable device, such as earbuds, smartwatch, smart glasses, or the like. Movement monitor 112, based on the data derived from the sensor-generated signals, can determine contextual parameters such as movement intensity, the number of erratic motions or jerking movements, the maximum and minimum accelerometer and gyroscopic values, a mean intensity of movements associated with intense activity, an estimated energy expenditure, movement entropy, and other motion-related parameters.

In certain arrangements, movement monitor 112 implements a machine learning model, such as a classification model (e.g., random forest). Movement monitor 112 generates a vector or higher-order tensor based on the motion data derived from the sensor-generated signals. The elements of the vectors or higher-order tensors comprise movement features. The machine learning model can be trained to classify an input vector or higher-order tensor, the classifying indicating a specific activity or posture of the user. For example, a random forest classifier implemented by movement monitor 112 can provide a fall detection mechanism by classifying certain movement features as likely indicating a user's accidental event such as a fall. Notwithstanding the model's predictive accuracy—greater than 95 percent by some estimates—there is an oft-unacceptable incidence of false positives or false alarms. Accordingly, as described below, system 100 incorporates additional features for verifying the model's prediction of a user fall or other adverse health event to militate against false positives. More generally, the machine learning model implemented by movement monitor 112 can identify the user's current activities by classifying real-time movements detected by the movement monitoring unit. Activity classifications determined by movement monitor 112 can include, for example, strenuous activity (e.g., intense exercise), brisk activity (e.g., stair climbing), moderate activity (e.g., walking), and resting (e.g., sitting, lying). In certain embodiments, the machine learning model implemented by movement monitor 112 can be trained to classify movements specific to the user based on the motion features captured over time by monitoring the user with various sensors of a device worn or carried by the user.

Context-aware anomaly determiner 102 generates a current context profile of the user by aggregating data derived by and received from vital signs monitor 108, environment monitor 110, and movement monitor 112. The current context profile provides a real-time, quantitative snapshot of the user's physiological state or condition, current activity, and present environment. The context-aware profile is a data structure. In certain arrangements, the data structure comprises an array, such as a matrix or higher-order tensor, whose elements correspond to a series of physiological measurements, or user vital signs (e.g., respiration rate, heart rate), and user movements captured by sensors over a predetermined span of time at certain intervals (e.g., 10-minute intervals).

Figure 2:
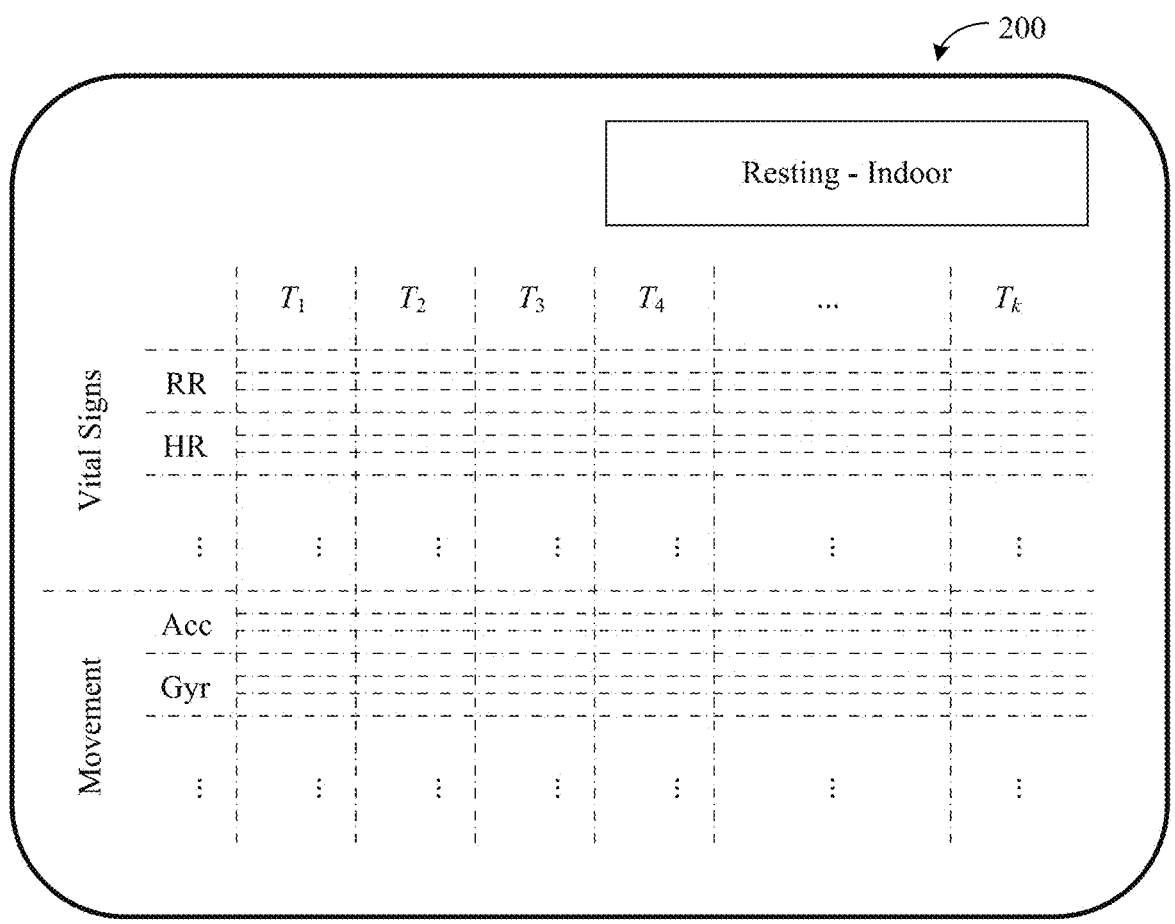
FIG. 2 illustrates an example current context profile generated by the system of FIG. 1.

Referring additionally to FIG. 2, example current context profile 200 is depicted. Illustratively, current context profile 200 is a matrix having a set of rows that comprise features corresponding to the user's vital signs, including respiration rate (RR) and heart rate (HR). These rows are concatenated with rows of movement features, including acceleration (Acc) and gyroscopic orientation (Gyr) features. The columns of current context profile 200 correspond to times, $T_1$, $T_2$, ..., $T_K$. Thus, illustratively, context-aware profile 200 is a time-series matrix whose elements correspond to a series of physiological measurements, or user vital signs, and user movements captured by sensors over a predetermined span of time. Context-aware anomaly determiner 102 determines the specific context based on the user's current activity as determined, for example, by the machine learning model classification of the user's movement, as well as based on the user's location and environment as determined, for example, from the user's GPS-determined geolocation and other environmental parameters determined by environment monitor 110. Illustratively, the specific context of current context profile 200 corresponds to the activity "resting" and location "indoors."

Current context profile 200 illustrates an efficient data structure for continuous or semi-continuous passive monitoring of the user's context-specific physiological state or condition. For example, at a given time interval the earliest elements of the time-series matrix—the first column under $T_1$—can be discarded and each remaining column shifted leftward to add the most recently determined features (vital signs and movements) inserted as the last column under $T_K$.

Referring still to FIG. 1, context-aware anomaly determiner 102 performs context-based anomaly detection 138 by comparing features of user's current context profile 200 to corresponding features of a context-aware baseline profile having the same context as the user's current context profile. Context-aware anomaly determiner 102 can perform the comparison in response to detecting a significant change in one or more of the user's vital signs (e.g., heart rate, respiration rate) monitored at different times, $T_K$ and $T_{K+1}$. Alternatively, context-aware anomaly determiner 102 can perform the comparison at each discrete interval (e.g., 10-minute intervals) of monitoring the user's vital signs and updating the user's vital signs to generate current context profile 200 of the user.

Figure 3:
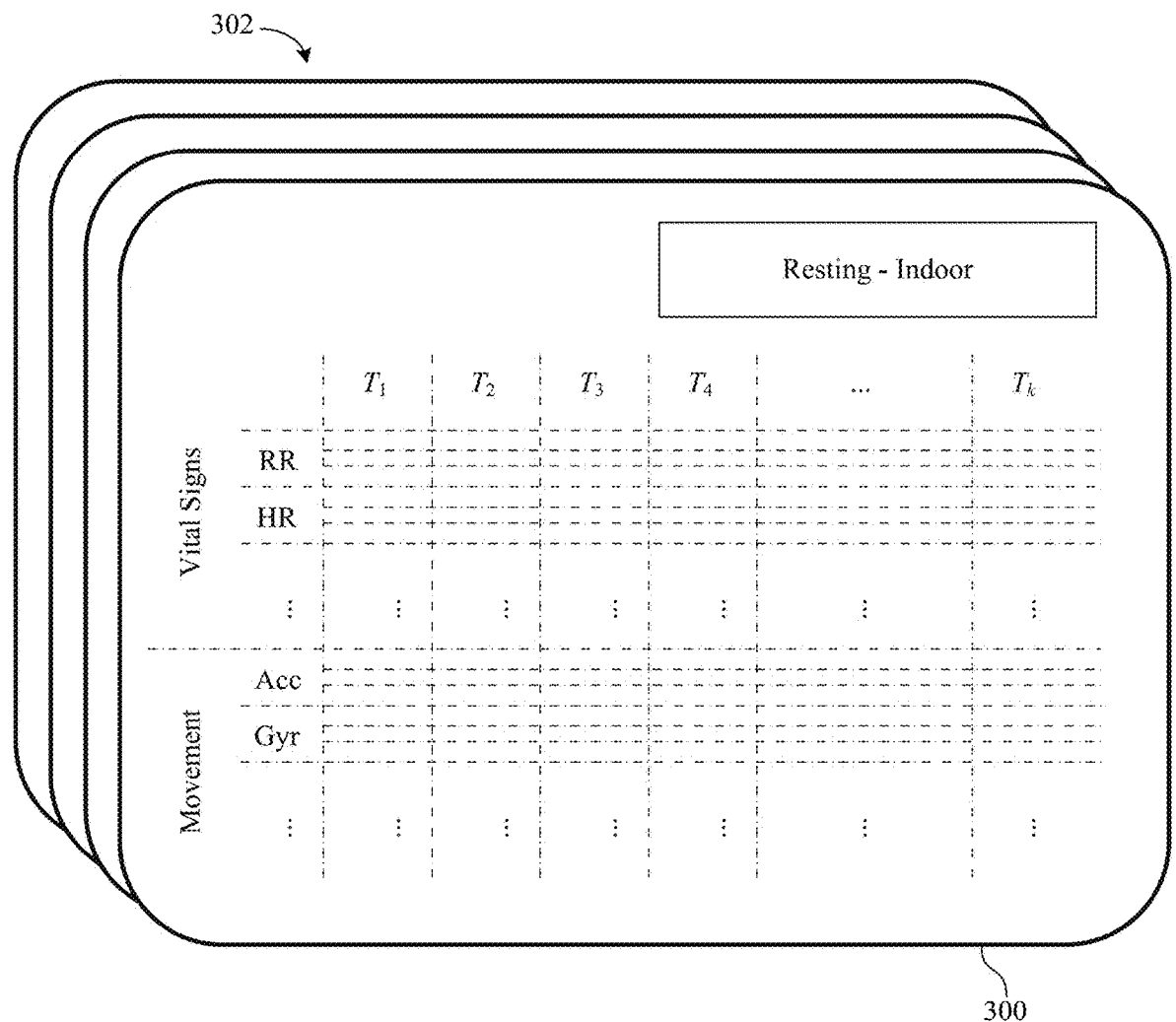
FIG. 3 illustrates an example collection of context-aware baseline profiles generated by the system of FIG. 1.

Referring additionally now to FIG. 3, context-aware anomaly determiner 102 selects context-aware baseline profile 300 having the same context as the user's current context profile 200 from a plurality of context-aware baseline profiles 302 having different contexts. Although illustratively the plurality of context-aware baseline profiles 302 includes only four context-aware baseline profiles, the plurality can, and typically does, include a much greater number of context-aware baseline profiles having different contexts. For example, if a context is characterized by J locations, K environments, and L activities, then the plurality can comprise as many as J×K×L context-aware baseline profiles having different contexts.

Context-aware anomaly determiner 102 performs context-based anomaly detection 138 by performing a row-by-row, feature-by-feature comparison of corresponding features of current context profile 200 and context-aware baseline profile 300 having the same context. In certain arrangements, context-aware anomaly determiner 102 constructs a null distribution for each row of the context-aware baseline profile 300 based on values of computed as cumulative sum (CuSum) statistics. CuSum statistics incorporate current and prior data to provide enhanced detection of shifts in a process and are thus well-suited for health data analysis. CuSum statistics for each column of current context profile 200 are evaluated. If a CuSum statistic for the i-th row, j-th column of the matrix representation of current context profile 200 deviates significantly from the null distribution—that is, by more than a predetermined threshold (e.g., greater than 1.5 standard deviations)—then context-aware anomaly determiner 102 flags the deviation as an anomaly.

Figure 4:
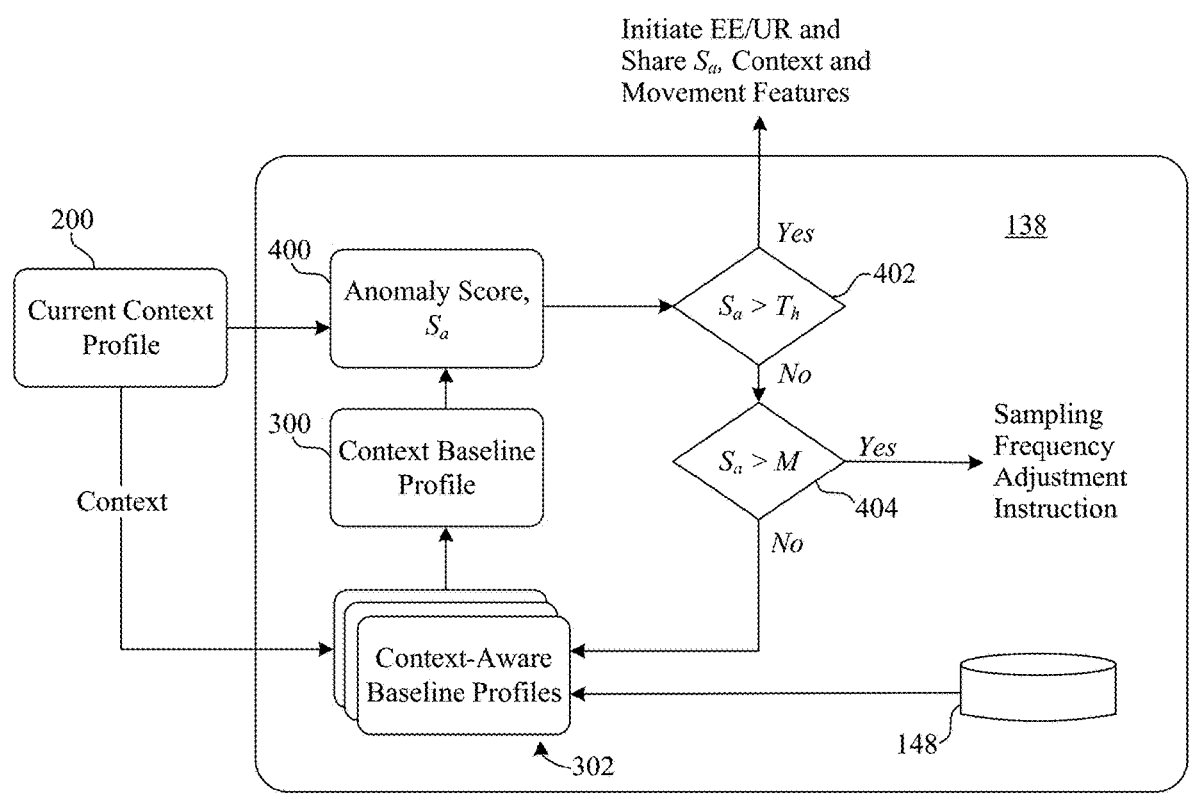
FIG. 4 schematically illustrates an example of context-based anomaly detection performed by the system of FIG. 1.

FIG. 4 schematically illustrates an example of context-based anomaly detection 138 performed by context-aware anomaly determiner 102 in accordance with certain embodiments. Context-aware anomaly determiner 102 extracts contextual information from current context profile 200. Based on the contextual information, context-aware anomaly determiner 102 selects context-aware baseline profile 300 from context-aware baseline profiles 302 electronically stored in database 148. Context-aware anomaly determiner 102 determines anomaly score $S_a$ 400 based on the CuSum statistics generated from a row-by-row, feature-by-feature comparison of current context profile 200 and context-aware baseline profiles 302. Context-aware anomaly determiner 102 determines a row-based score $W_{mi}$ for each column $T_1$ through $T_K$ of current context profile 200, where m indicates a specific context and i indicates the row of a given column and each column corresponds to a specific time. Assuming current context profile 200 is an N×K matrix, context-aware anomaly determiner 102 computes a score $w_{m\cdot j}$ by summing the rows of each column j to determine a count of the anomalies detected at time $T_j$. An anomaly is detected at the i-th row of the j-th column if the value deviates significantly from the null distribution. For each column $T_1$ through $T_K$ of current context profile 200, the summation of significant deviations from the null distribution is:

$$w_{m\cdot j} = \Sigma_{i=1}^{N} c_{mij}$$

where N is the number of rows of the j-th column corresponding to time $T_j$ and $$c_{mij} = \begin{cases} 1, & \text{if anomaly detected} \\ 0, & \text{otherwise.} \end{cases}$$

Summing each column's count of anomalies yields anomaly score $S_a$ 400:

$$S_a = \Sigma_{j=1}^{K} w_{m\cdot j}.$$

Based on anomaly score $S_a$ 400, context-aware anomaly determiner 102 determines an action in accordance with the following rules:

(1) If, at decision 402, $S_a > T_h$, where $T_h$ is a predetermined high threshold indicating the occurrence of a possible abnormal health event, context-aware anomaly determiner 102 initiates an event confirmation procedure performed as described below by EE/UR determiner 104. Context-aware anomaly determiner 102 also conveys to EE/UR determiner 104 the $S_a$, context information, and movement features; and (2) If, at decision 404, $S_a < T_h$ but $S_a > M$, where M is a predetermined low threshold, context-aware anomaly determiner 102 conveys an instruction to vital signs monitor 108, and movement monitor 112 to increase the frequency (e.g., increase from 10-minute intervals to 1-minute intervals) with which each collects and processes data derived from signals generated by the sensors monitoring the user's vital signs and movements. Otherwise, context-aware anomaly determiner 102 optionally updates the baseline data for the user but initiates no further action.

Referring again to FIG. 1, if anomaly score $S_a$ 400 is greater than the high threshold $T_h$ such that context-aware anomaly determiner 102 invokes the procedures performed by EE/UR determiner 104, then EE/UR determiner 104 responds by conveying a recording request to multimedia sensor handler 114 operatively coupled with one or more of multimedia sensors 140. Multimedia sensors 140 illustratively include microphone 142 for recording the user's voice and other sounds, camera 144 for recording user movements, and eye tracker 146 for tracking eye movements of the user. In response to the recording request conveyed by EE/UR determiner 104, multimedia request handler 116 invokes operation of one or more of multimedia sensors 140 to collect at least one multimedia event. A multimedia event can include, for example, breathing sounds or speech of the user, the user's movement or posture, eye movements of the user, or other such events captured by multimedia sensors 140. Multimedia data handler 118 extracts features from the multimedia sensors for input into one or more machine learning models implemented by EE/UR determiner 104.

In certain arrangements, the one or more machine learning models implemented by EE/UR determiner 104 are trained to classify various multimedia events based on the features extracted by multimedia data handler 118. Examples audio-based multimedia event recordings include a user's agonal breathing, breathlessness, groans or other pain-relate sounds, unintelligible speech, or the like. Examples of camera-captured multimedia events include video showing the user failing to get up after falling, sweating heavily, not moving at all, or other abnormal movement. Each audio-based and camera-captured multimedia event detected and classified according to the machine learning model generates event input $a_i$, which as described below, is used by EE/UR determiner 104 in generating an emergency event score, $S_{EES}$. As already noted, emergency events also can be associated with abnormal body movements detected by movement monitor 112. Movement data generated by movement monitor 112 can also be classified by a machine learning model, as described above. Classification of the movement data can correspond, for example, to the user experiencing convulsions, taking a fall, exhibiting abnormal gaits or postures, or other abnormal movement. Each such event detected and classified according to the machine learning model can generate an event input $b_i$ that also is used by EE/UR determiner 104 to generate an emergency event score.

EE/UR determiner 104 generates emergency event score $S_{EES}$ by taking a sum of highly abnormal event score $S_h$ and abnormality score $S_a$ and a summation of the products of events $a_i$ and $b_i$ times the negative log-probabilities of the events $a_i$ and $b_i$:

$$S_{EES} = S_h + S_a + \sum_{i=1}^{n} -\log(P_{ei}) \cdot e_i$$

where $P_{ei}$ is the probability of an occurrence of event $e_i$, and $e_i = a_i$ or $e_i = b_i$. Probabilities $P_{ei}$ can be predetermined based on empirical evidence and electronically stored in database 148. Highly abnormal event score $S_h$ is based on predetermined values generated in response to certain highly abnormal events. These highly abnormal events can include, for example, a fall, very high body temperature (e.g., greater than 103 F), low blood oxygen saturation (e.g., less than 90 percent), abnormally high resting heart rate (e.g., greater than 120 bpm), abnormally high resting respiratory rate (e.g., greater than 30 cycles per minute), and the like.

Figure 5:
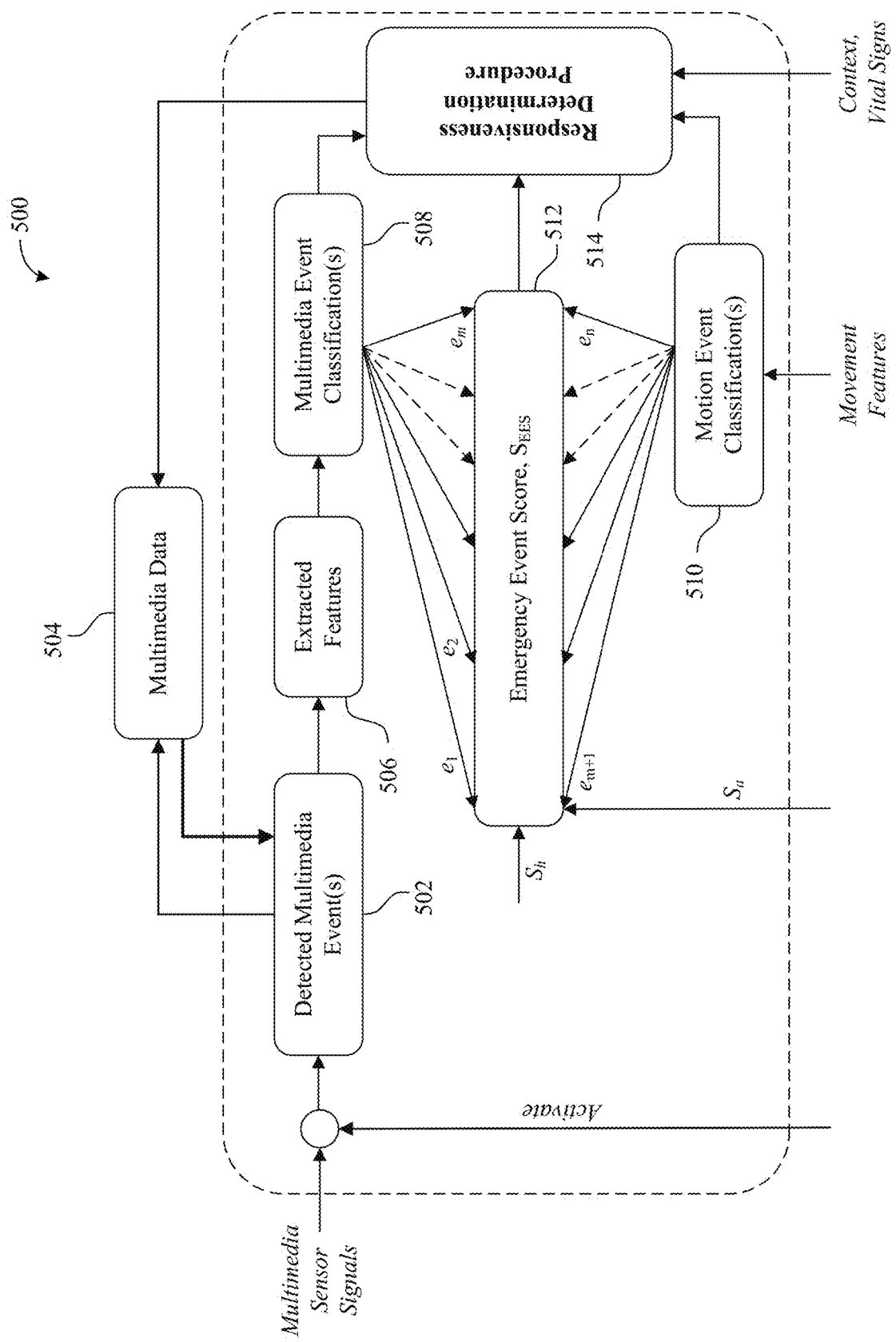
FIG. 5 schematically illustrates an example of emergency event scoring performed by the system of FIG. 1.

FIG. 5 schematically illustrates an example of emergency event scoring 500 performed by EE/UR determiner 104 in generating emergency event score $S_{EES}$. In response to a recording request conveyed by EE/UR determiner 104, one or more multimedia events 502 is detected from signals generated by multimedia sensors. Multimedia data 504 is derived from detected multimedia event(s) 502. Extracted features 506, features extracted from detected multimedia events 502, are input to a machine learning model classifier for generating one or more multimedia event classifications 508. Multimedia event classification(s) 508 can be combined with motion event classification(s) 510 made by movement monitor 112 to generate multimedia event inputs $e_1, \ldots, e_m$ and motion events $e_{m+1}, \ldots, e_n$, respectively. As described above, emergency event score $S_{EES}$ is a summation of the products of the negative log-probabilities times the values of each of multimedia event inputs $e_1, \ldots, e_m$ and motion events $e_{m+1}, \ldots, e_n$, which is added to the sum of highly abnormal event score $S_h$ and abnormality score $S_a$. If $S_{EES}$ is greater than a predetermined emergency threshold R indicating the likelihood of an emergency event, then EE/UR determiner 104 performs user responsiveness determination procedure 514 and, depending on the determination, may take other actions.

Optionally, with each updating of the user's current context profile, system 100 can run one or more priority checks to determine whether, based on the user's vital signs and/or movements, one or more highly abnormal events have been detected that immediately invoke responsiveness determination procedure 514. The values generated in response to the detection of such highly abnormal events can be set so that highly abnormal score $S_h$ is invariably high enough a score to ensure that $S_{EES}$ is greater than emergency threshold R, thus automatically invoking responsiveness determination procedure 514. In certain arrangements, system 100 is configured to enable the user to specifically designate highly abnormal events, the detection of which automatically invokes responsiveness determination procedure 514 and, if needed, an emergency response. For example, an elderly user who is likely to be severely debilitated by a fall can designate such as a highly abnormal event. When motions are detected that a machine learning model classifies as corresponding to a fall, the resulting abnormal event score $S_h$ is such that $S_{EES}$ is invariably greater than emergency threshold R and responsiveness determination procedure 514 is automatically invoked. An individual who is prone to seizures, for example, can designate such as a highly abnormal event so that when motions are detected that the machine learning model classifies as corresponding to a seizure, abnormal event score $S_h$ is such that it, too, automatically invokes.

Figure 6:
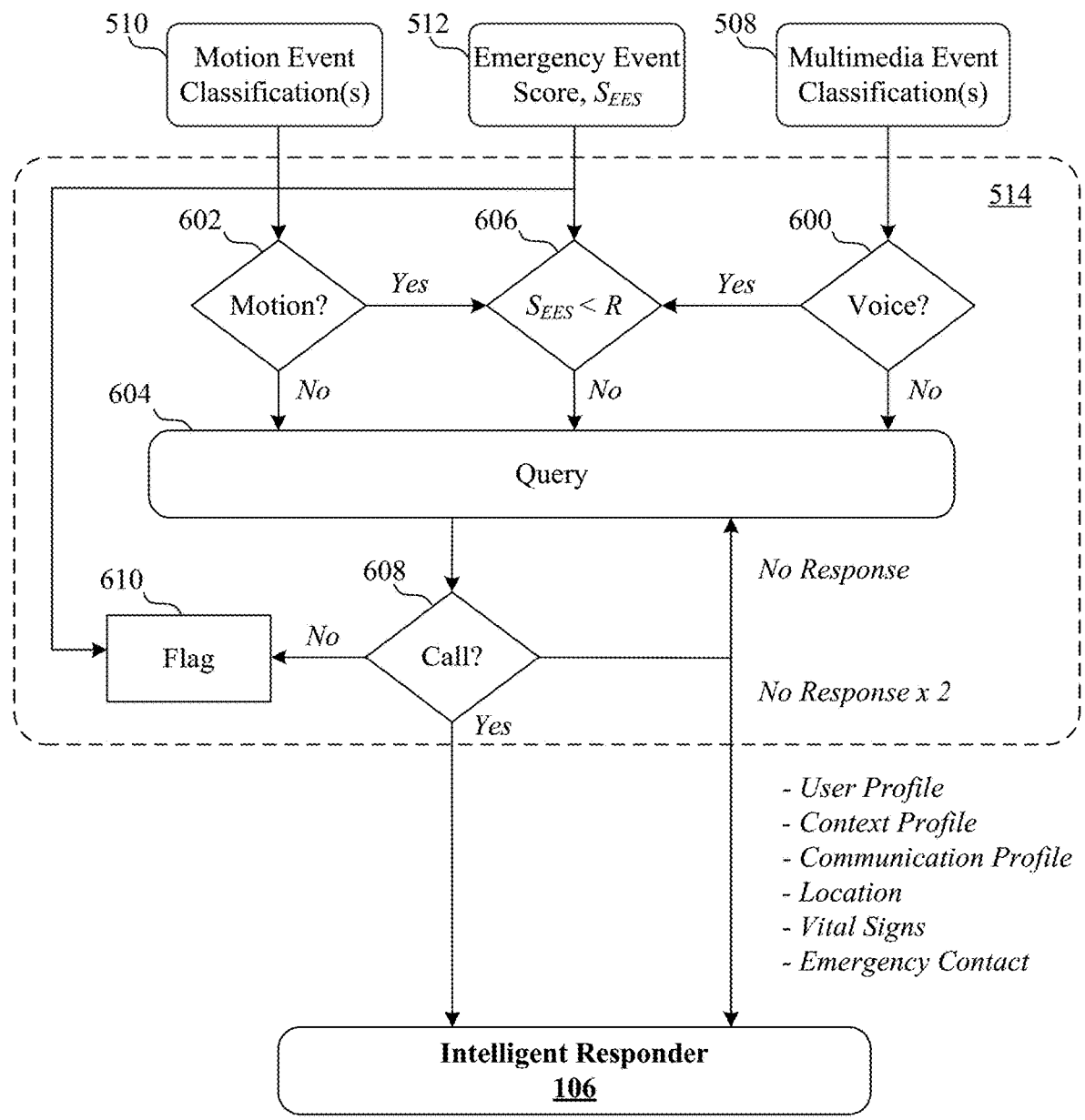
FIG. 6 schematically illustrates an example of user responsiveness determination performed by the system of FIG. 1.

FIG. 6 schematically illustrates an example of user responsiveness determination procedure 514 (FIG. 5) performed by EE/UR determiner 104 in accordance with certain arrangements. EE/UR determiner 104 can determine whether at decision 600 there is voice activity based on multimedia event classification(s) 508 or whether at decision 602 there is movement of the user based on motion even classification(s) 510 (FIG. 5). In the event that there is either no voice activity at decision 600 or no motion detected at decision 602, then EE/UR determiner 104 pushes query 604 to the user asking whether system 100 should initiate call 608 requesting emergency assistance. Even if both voice activity and motion are detected, but $S_{EES}$ at decision 606 is greater than emergency threshold R, then EE/UR determiner 104 nonetheless pushes query 604 to the user. Query 604 asks the user whether the user needs assistance. If at decision 608 the user responds 'No' to query 604 or if $S_{EES}$ is less than emergency threshold R, EE/UR determiner 104 generates flag 610 and applies it to the event-related data indicating the event is not an emergency event. If the user responds 'Yes' to query 604 at decision 608 or does not respond after a pre-set number of queries (e.g., two attempts), EE/UR determiner 104 initiates action by intelligent responder 106. Optionally, EE/UR determiner 104 also can convey to intelligent responder 106 additional data relevant to the likely emergency. The data can include, for example, a user profile, current vital signs, context information, location information, contact information, and/or other information that would be relevant and useful to an emergency responder.

If invoked by EE/UR determiner 104, intelligent responder 106 utilizes the communication capabilities of the device in which system 100 is implemented to make an automated call to an emergency contact. For example, if system 100 is implemented in a wearable device (e.g., earbuds, smartwatch, smart glasses), the device may include a wireless communication subsystem, such as wireless communication subsystem 1324 of device 1300 (FIG. 13), with which intelligent responder 106 can place the call to the emergency contact. Alternatively, if the device in which system 100 is implemented lacks a communication capability, the device can communicatively couple to another of the user's devices (e.g., smartphone) that can be used by intelligent responder 106 to place the call to the emergency contact.

Intelligent responder 106 can make an automated call or send a text message to an emergency medical service (EMS) and/or to a predesignated emergency contact. Based on system-generated GPS location data, intelligent responder 106 can place the automated call or send the text message to the EMS nearest to the user's current location. Likewise, if the user has electronically stored in database 148 a list of predesignated names of multiple emergency contacts, intelligent responder 106 can search for and select the one nearest to the user's current location to place a call to or send a text message. Optionally, the user can specify that one or more contacts, such as a physician or family member, are to be contacted by intelligent responder 106 regardless of the user's location relative to the pre-specified contact(s). In each instance, intelligent responder 106 can convey a prerecorded voice or text message and append information such as the user's location and a summary of the user's current vital signs.

In some arrangements, health professionals can register their information in a global database and input their qualifications along with supporting documentations. Having verified the user's emergency health event, intelligent responder 106 can convey a notification to a registered professional that, based on GPS or other geolocation data, intelligent responder 106 determines is near the user's current location. In a particular arrangement, multiple adverse health event detection and response system users also may agree to link to a common communication network, such as central server, to be contacted if nearby to another user who experiences an emergency health event. Such an individual may be able to render at least limited assistance until the arrival of a health professional.

System 100 can establish a communication link between the device in which system 100 is implemented and another device used by either an EMS dispatcher or an emergency contact. Via the communication link, intelligent responder 106 can maintain contact with, and provide updates on the user to, the EMS dispatcher and/or other emergency contact. In addition to notifying an EMS dispatcher, emergency contact, and/or nearby user, intelligent responder 106 can also convey information useful in rendering medical assistance. In certain arrangements, intelligent responder 106 generates a summary of the context-based information of the user. This can include the user's current vital signs, recent activities, and any previous or current movements indicative of the user's current physiological state or condition. Via the established communication link between the device in which system 100 is implemented, or communicatively coupled via a companion device, that of an EMS dispatcher or other health professional, the EMS dispatcher or other health professional can request that system 100 use data derived from multimedia sensors 140 and processed by multimedia sensor handler 114 to collect and convey current information on the user. For example, if the dispatcher needs to evaluate the user's current physiological condition, the dispatcher can request live audio and/or video of the user in addition to the user's vital signs.

Using GPS data, intelligent responder 106 can estimate a time until arrival of an ambulance as well as a distance between the user and a health professional. For example, in remote areas, where an available ambulance is not located nearby, intelligent responder 106 can convey a help request to a system-registered health provider or user able to render at least limited assistance until an ambulance can reach the user.

During an emergency, system 100 can increase the frequency that the user's current context profile is updated such that the monitoring is continuous or nearly so. Ordinarily, however, continuous, or nearly continuous, monitoring may be inefficient. But because a user-specific set of context-aware baseline profiles must typically be built over time through system 100's monitoring of the user, system 100—at least during an incipient phase of usage—may not have sufficient user-specific data to build a complete set of snapshots of the user's baseline in different contexts. For example, during much of the time, a typical user may be sedentary or otherwise engaged in activities that do not involve much physical exertion by the user. Thus, initially at least, system 100 may have only a partial set of context-aware baseline profiles of the user corresponding to a limited number of contexts. Accordingly, in certain arrangements, system 100 implements collaborative filtering to generate a temporary, but extended, set of context-aware profiles for the user based on data corresponding to other users identified as demographically similar to the user.

System 100 can acquire data corresponding to other users identified as demographically similar from a global database of context-aware baseline profiles. In certain arrangements, system 100 identifies demographically similar users by computing a similarity matrix wherein similarity $\text{Sim}_{(x,y,c)}$ for any two users can be calculated, for example, using a Pearson correlation:

$$\text{Sim}_{(x,y,c)} = \frac{\sum_i (F_{x,i} - \overline{F}_x)(F_{y,i} - \overline{F}_y)}{\sqrt{\sum_{i=1}^k (F_{x,i} - \overline{F}_x)^2} \sqrt{\sum_{i=1}^k (F_{y,i} - \overline{F}_y)^2}}$$

where 'x' and 'y' correspond to different users within the same context 'c' and $F_i$, i=1, . . . , k, are context-specific features (e.g., vital signs, movements). Based on a similarity matrix calculation, system 100 identifies similar users using the k-nearest neighbor algorithm. Context-aware baseline profiles of the similar users are then estimated from a weighted average of context-specific features (e.g., vital signs, movements) of each of the similar users.

An at-large population of users can be divided into two or more user groups based on epidemiological, demographic, and/or other health-related factors. Thus, in accordance with some arrangements, the user of system 100 can be assigned to one of multiple different priority groups based on factors specific to the user. For example, the user may be assigned to a high-risk group. The assignment can be based, for example, on factors such as age (e.g., greater than 55), medical history (e.g., number of hospitalizations), health-related events like cardiac arrest, lung or kidney ailments, cancer, and/or other factors determined based on epidemiological evidence to place a user at higher risk. In certain arrangements, system 100 can utilize a device portal to enable a medical professional (e.g., the user's physician) to assign the user to a specific risk group. Users with no previous history of a significant medical events or underlying abnormal health condition can be assigned to a low-risk user group. Overtime, based on the updating of the user's context-aware profile, system 100 can recommend that the user be re-assigned to a different group. For example, system 100 can recommend that a user be re-assigned to a high-risk group in response to the user suffering one or more adverse health events or in response to a sustained change in one or more of the user's vital signs with respect to a given context. As noted above, system 100 can update user's baseline profiles each time that a possible adverse event is detected but does not give rise to an emergency event.

Depending on the risk group to which the user is assigned, system 100 can adjust one or more parameters for determining whether the user has likely experienced an adverse or emergency health event based on the emergency event score $S_{EES}$. If the user is classified as at-risk, then system 100 can apply relatively higher weights to one or more of the values used to determine abnormality Score $S_a$ and highly abnormal even score $S_h$. For example, if the user has a prior history of heart attacks, system 100 applies a higher weighting to heart-related features. More generally, system 100 can set lower thresholds for M, $T_h$, and R for detecting an adverse health event or an emergency health event. In other arrangements, system 100 can determine $S_{EES}$ based on a user-specific risk factor $r_p$ and, optionally, a context-specific risk factor $r_c$:

$$S_{EES} = (r_p + r_c) \cdot (S_h + S_a + \Sigma_{i=1}^n -\log(P_{ei}) \cdot e_i).$$

The user-specific risk factor $r_p$ can be calculated based on the user's physiological or medical condition. The context-specific risk factor $r_c$ can correspond to a specific context but when combined with the user-specific risk factor $r_p$ also can reflect a condition or state of the user. For example, user-specific risk factor $r_p$ may be higher for a user having a heart condition than for a user who does not. Context-specific risk factor $r_c$ may be higher for heavy exercise as distinct from a more sedentary activity. When both risk factors are combined, such as for a user having a heart condition who is engaging in heavy exercise, $S_{EES}$ is commensurately greater than it is for a healthy user who is sedentary.

System 100 optionally includes a context-aware privacy manager that allocates sensing resources in response to activation requests by vital signs monitor 108, environment monitoring unit 110, movement monitor 112, and multimedia sensor handler 114. The context-aware privacy manager can apply a rule-based approach to allocate sensing resources according to whether the request relates to monitoring the user experiencing a possible emergency event or for a continuous monitoring of the user. In certain arrangements, the context-aware privacy manager updates and maintains a priority queue for each context and allocates sensing resources accordingly.

FIG. 7 illustrates example rule set 700 applied by the context-aware privacy manager for updating and maintaining the priority queue. Illustratively, the context-aware privacy manager responds to a possible emergency event by allocating motion sensors 136 and multimedia sensors 140 to continuous sensing and continuous recording of motion and multimedia data derived from signals generated by the sensors. Otherwise, for continuous sensing, the context-aware privacy manager allocates motion sensors 136 to continuous sensing and continuous recording of motion data generated, but multimedia data is generated and recorded only once every 10 minutes, thus limiting the use of more resource-intensive multimedia sensors and related signal processing. The main, the context-aware privacy manager allocates motion sensors 136 for vital sign monitoring. Motion sensors 136, however, can introduce an inordinate number of motion artifacts, which can yield inaccurate or unreliable motion data. Accordingly, the context-based sensor scheduler can apply additional pre-established rules. Firstly, if the user is performing a motion-intense activity, thus rendering motion sensors 136 less reliable, the context-aware privacy manager allocates multimedia sensors 140 to more frequent user monitoring. However, because monitoring using multimedia sensors 140 tends to be relatively more privacy invasive, the context-based sensor scheduler will in most circumstances enforce less frequent multimedia sensor-based monitoring. Secondly, therefore, if the user is sedentary or stationary, then the context-aware privacy manager limits monitoring by multimedia sensors 140, limiting the frequency to that sufficient to enhance the reliability of motion sensors 136 engaged in vital signs monitoring. For example, the frequency can be limited to intermittent monitoring at regular intervals (e.g., at 10-minute intervals).

Figure 8:
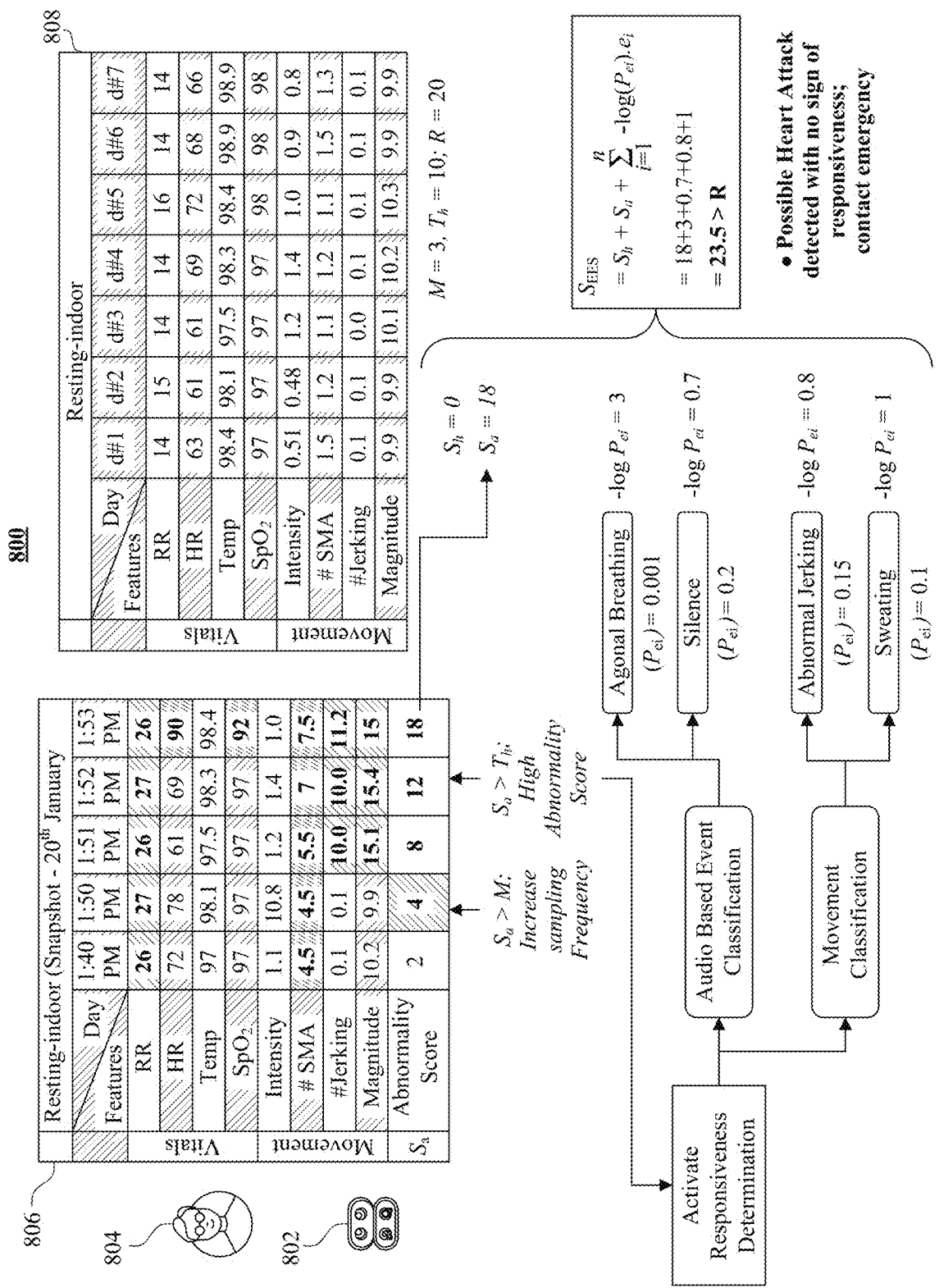
FIG. 8 illustrates certain operative aspects of the system of FIG. 1.

FIG. 8 illustrates certain operative aspects 800 of system 100. Illustratively, system 100 is implemented in earbuds 802 worn by user 804. User 804 is a 75-year-old male who has had a heart attack, has high-blood pressure, is overweight, and a smoker. Classifying user 804 as high risk, system 100 applies low threshold M=3, high threshold $T_h$=10, and emergency threshold R=20. System 100 illustratively updates current context profile 806 based on signals generated by one or more sensors and selects context-aware baseline profile 808 having the same context (resting-indoor) for comparison. Although current context profile 806 and context-aware baseline profile 808 are illustrated by 10×5 matrices, it is expressly noted that both can, and typically will, comprise matrices having a much greater number of elements. Initially at times 1:40 PM and 1:50 PM, the first row of current context profile 806 indicates higher than baseline respiration rates (RRs) and the sixth row indicates abnormal body movements. System-determined abnormality score $S_a$ exceeds low threshold M but is less than high threshold $T_h$, prompting context-aware anomaly determiner 102 to increase monitoring frequency. With increased monitoring frequency, additional abnormal movements are detected as well as continuing abnormal respiration rates, leading to abnormality scores of 8 and 12 at times 1:51 PM and 1:52 PM, respectively. The abnormality score $S_a$ of 12 exceeds threshold $T_h$, to which EE/UR determiner 104 responds to the possibly abnormal event by initiating a confirmation procedure. The procedure yields multimedia (audio-based) event and movement classifications. Multimedia event classifications correspond to agonal breathing and lack of vocalization, as well as sweating. Movement event classifications correspond to abnormal jerking. At the point that the latest (last matrix column) set of features are combined at 1:53 PM with prior ones, the $S_{EES}$ score is above emergency threshold R. In this example, system 100 confirms a likely emergency event (possible heart attack).

Once the emergency event is confirmed by EE/UR determiner 104, intelligent responder 106 initiates remedial action, as described above.

Figure 9:
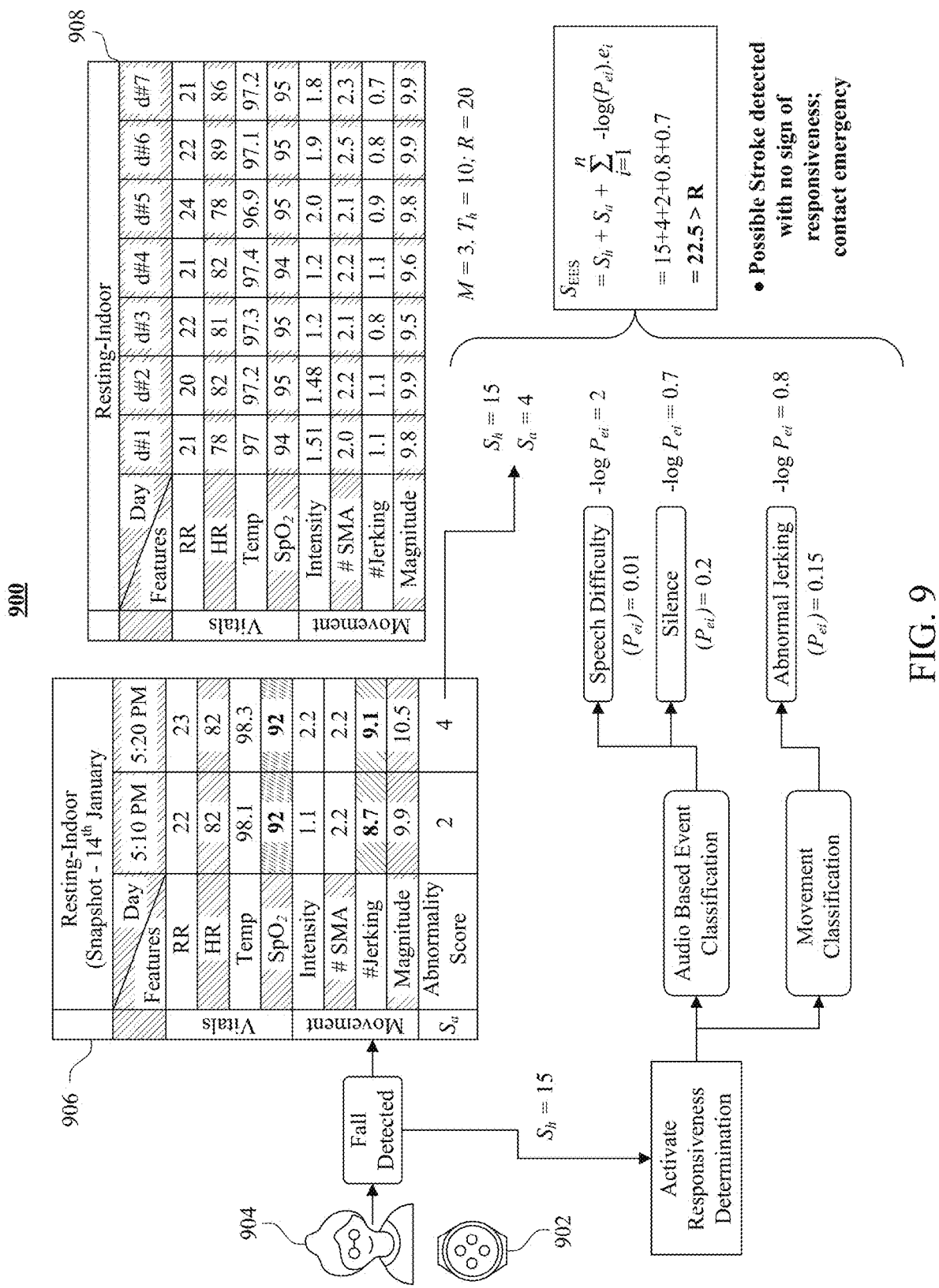
FIG. 9 illustrates certain operative aspects of the system of FIG. 1.

FIG. 9 also illustrates certain operative aspects 900 of system 100. Illustratively, system 100 is implemented in smartwatch 902 worn by user 904. User 904 is a 70-year-old female who is classified by system 100 as high risk owing to her having heart disease, diabetes, and high cholesterol. Accordingly, the same thresholds apply as illustrated in FIG. 8. Illustratively, an IMU of smartwatch 902 generates a signal that system 100 (using the machine learning described above) classifies as a fall, which is predesignated as a highly abnormal event with a highly abnormal event score $S_h$ of 15 and which automatically invokes an immediate user responsiveness determination by EE/UR determiner 104. The determination generates the abnormality score $S_a$ based on the most recent updating of current context profile 906 based on comparison with context-aware baseline profile 908, as well as event classifications (also made using machine learning models) of audio-based multimedia events movement events. The audio-based multimedia event classifications correspond to speech difficulty mixed with intervals of silence. The movement event classification corresponds to abnormal jerking. Based on the $S_h$ and $S_a$ scores and summation of the product of events times negative log-probabilities of the events, the $S_{EES}$ score (indicative of a possible stroke) as determined by EE/UR determiner 104 exceeds emergency threshold R. EE/UR determiner 104 responds by invoking remedial action by intelligent responder 106.

Figure 10:
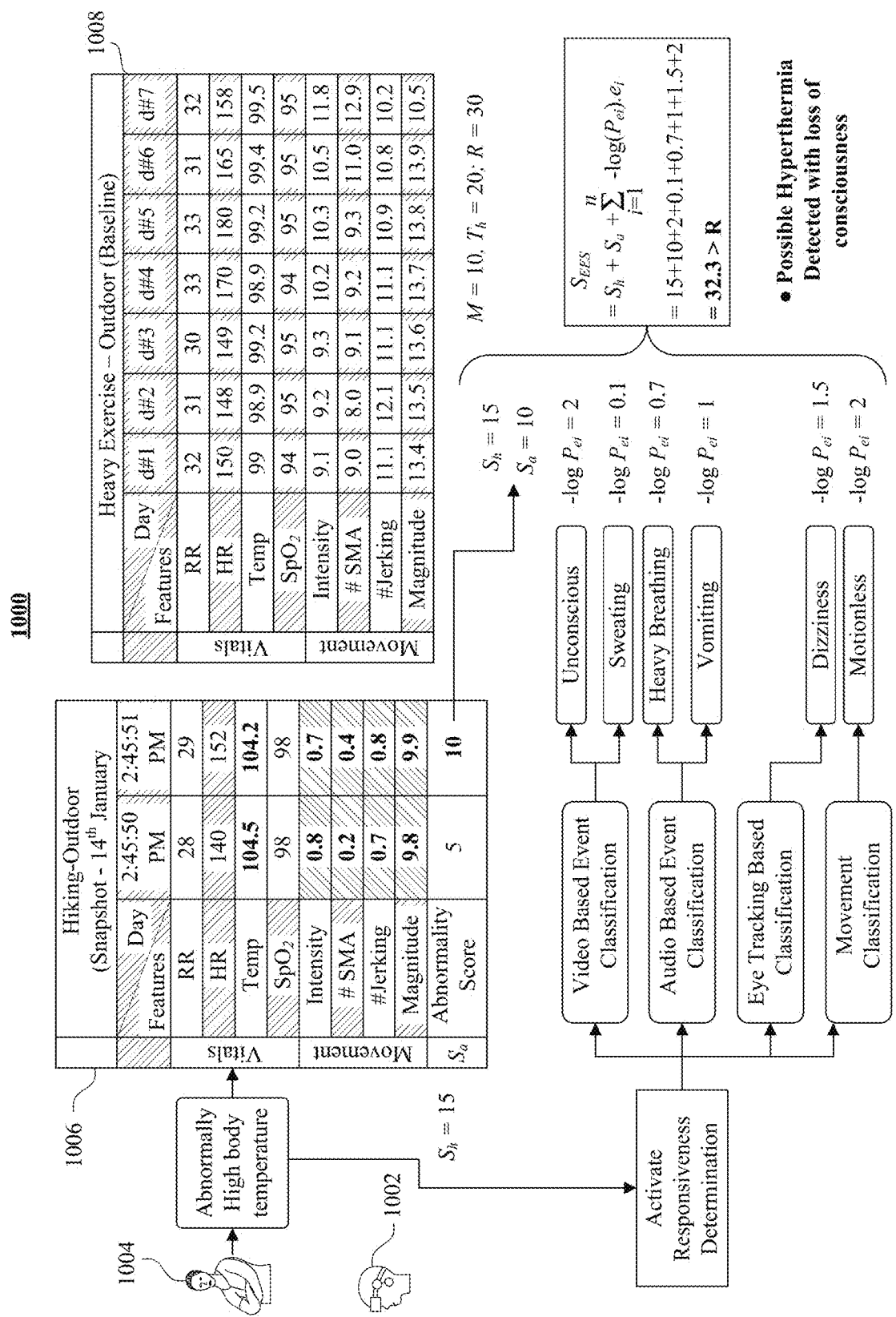
FIG. 10 illustrates certain operative aspects of the system of FIG. 1.

FIG. 10 also illustrates certain operative aspects 1000 of system 100. Illustratively, system 100 is implemented in smart glasses 1002 worn by user 1004. User 1004 is a healthy 30-year-old male who is classified by system 100 as low risk and is assigned values of 10, 20, and 30 for thresholds M, $T_h$, and R, respectively. Illustratively, body thermometer 128 of vital signs monitor 108 embedded in smart glasses 1002 detects a highly abnormal core body temperature for user 1004, which is predesignated as a highly abnormal event with highly abnormal event score $S_h$ of 15. Detection of user 1004's highly abnormal core body temperature yielding abnormal event score $S_h$ of 15 automatically invokes an immediate user responsiveness determination by EE/UR determiner 104. The determination generates the abnormality score $S_a$ based on the most recent updating of current context profile 1006 based on comparison with context-aware baseline profile 1008, as well as event classifications (also made using machine learning models). Video-based multimedia event classifications correspond to user 1004's unconscious state and sweating. Audio-based multimedia event classifications correspond to breathing heavily and vomiting. Eye tracking classification corresponds to dizziness, and movement event classification corresponds to a motionless state. As determined by EE/UR determiner 104, the $S_{EES}$ score (indicating possible hypothermia) (equal to the sum of $S_h$ and $S_a$ scores added to a summation of the product of each abnormal events times the negative log-probabilities of the events) exceeds emergency threshold R. E/UR determiner 104 responds by invoking remedial action by intelligent responder 106.

Figure 11A:
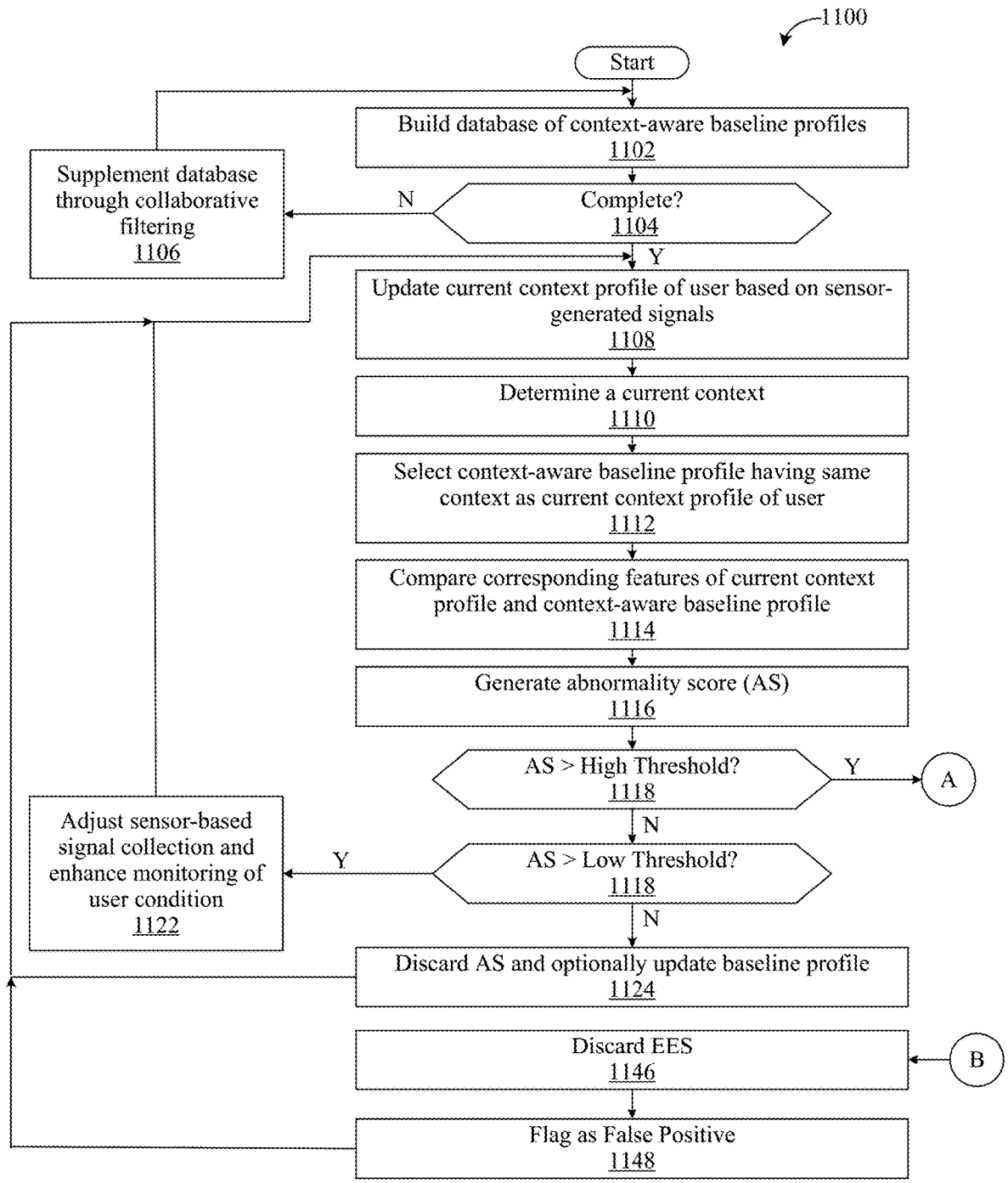
FIGS. 11A and 11B illustrate an example method of adverse health event detection and emergency response.
Figure 11B:
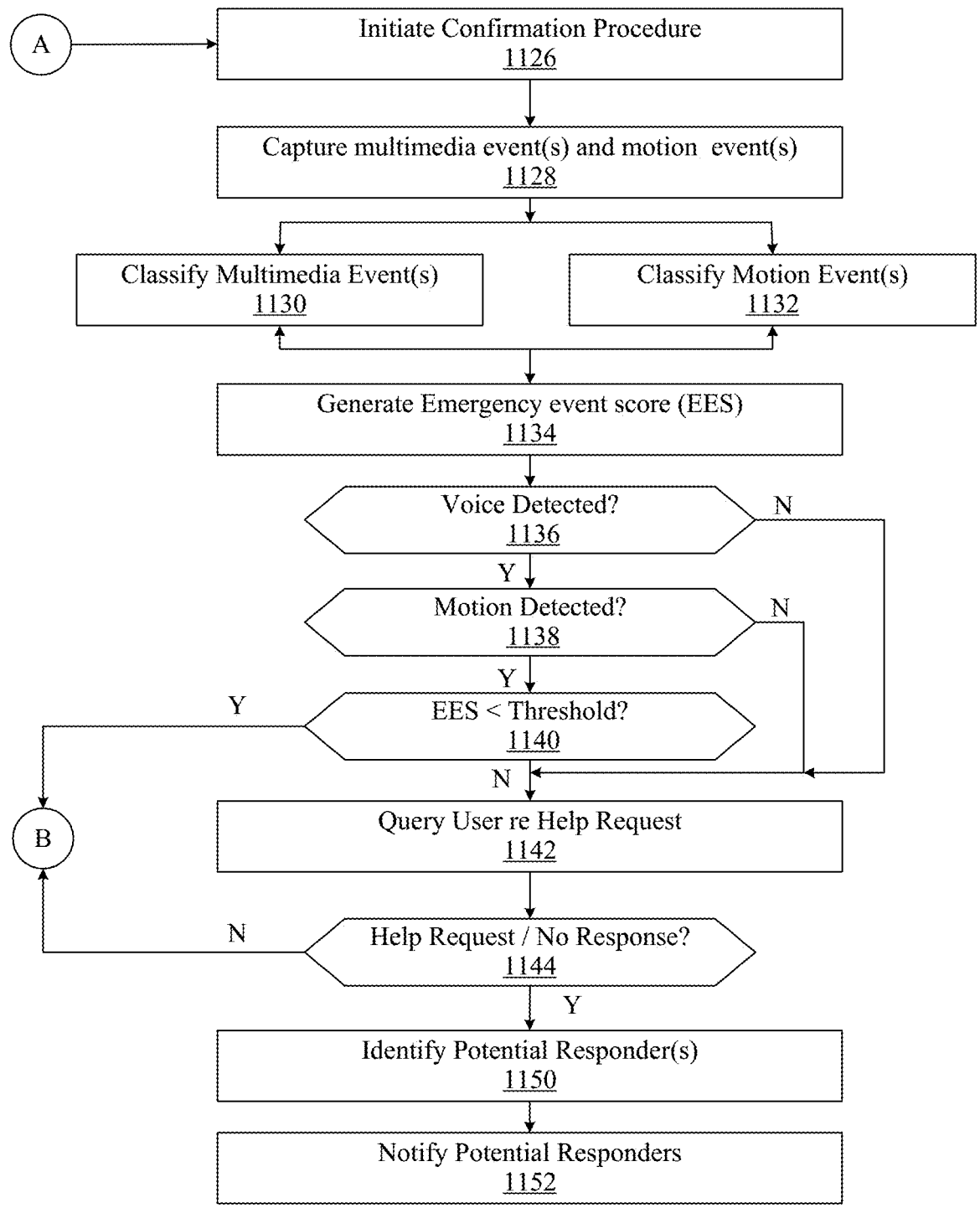

FIGS. 11A and 11B illustrate an example method 1100 of adverse health detection and emergency response. Method 1100 can be performed by a device (or device operatively coupled to a companion device) including an adverse health detection and emergency response system as described herein (collectively "the system").

At block 1102, the system can build a database of context-aware baseline profiles specific to the user. If at block 1104, the system determines that the database is as yet incomplete, then at block 1106 the system can supply missing data using data of similar users as needed. In some arrangements, the system implements collaborative filtering to generate a temporary, but extended, set of context-aware profiles for the user based on data corresponding to other users identified as demographically similar to the user. The system, in certain arrangements, identifies demographically similar users by computing similarity matrices and determining a statistical relationship such as the Pearson correlation between the user and other users to identify similar user. The building process can continue over time as the system revises the context-aware baseline profiles in response to sustained changes in the user's vital signs.

At block 1108, the system can update the user's current context profile. The updating can be based on signals generated by one or more sensors, the signals generated in response to one or more physically measurable phenomena associated with the user. The current context profile can include features corresponding to the user's vital signs—that is, measurable variables indicating a current physiological condition or state of the user—as well as data on the user's current activities, environment, and location. In certain arrangements, the system intermittently updates the current context profile at a frequency determined based on a risk category to which the user is assigned. The risk category can be determined based on user demographic data.

At block 1110, the system determines the context and at block 1112 selects a context-aware baseline profile having the same context as the current context profile. The context-aware baseline profile is selected from the database of multiple context-aware baseline profiles. Different context-aware baseline profiles correspond to different contexts.

At block 1114, the system compares features (matrix elements) of the current context profile with corresponding features of the selected context-aware baseline profile. One or more deviations of a feature of the current context profile from one or more corresponding features of the selected context-aware baseline profile can indicate that the user is experiencing an adverse health event, possibly one that arises to the level of a medical emergency.

In certain arrangements, the system determines a likely occurrence of an abnormal health event based on an abnormality score generated by the system at block 1116. In one aspect, the abnormality score can be determined based on CuSum statistics computed from each current context profile feature's deviation from a null distribution determined from the context-aware baseline profile.

At block 1118, if the abnormality score is less than a high threshold, then at block 1120 a determination is made whether the abnormality score is greater than a low threshold. If so, then because the abnormality score is less than the high threshold but greater than the low threshold, the system adjusts the sensor-based signal collection (e.g., increases the frequency of signal collection) at block 1122 to enhance monitoring of the user. By adjusting a frequency of intermittently updating the current context profile in response to a deviation between one or more corresponding features of the current context profile and the context-aware baseline profile, the system gathers information that may resolve uncertainty regarding the current physical condition of the use.

Otherwise, if at block 1120 a determination is made that the abnormality score is less than a low threshold at block, then at block 1124, the system discards the abnormality score. Optionally, the system can update the context-aware baseline profile on the assumption that the apparent disparity between the current context profile and context-aware baseline profile indicates a sustained change in certain vital signs of the user but not such as to indicate an abnormality (e.g., an unproblematic increase in average blood pressure corresponding to an increase in the user's age).

If at block 1118 the abnormality score is greater than the high threshold, the score indicates a likely serious health event, possibly one rising to the level of a medical emergency. To both gain greater information about the user's actual physical condition and to lessen the likelihood of a false positive. The system, at block 1126 initiates a confirmation procedure. An aspect of the confirmation procedure is capturing multimedia events with multimedia sensors and motion events with motion sensors at block 1128.

At blocks 1130 and 1132, respectively, the system classifies the multimedia events and motion events using one or more machine learning classification models (e.g., random forest). The classifications identify one or more abnormal or highly abnormal events.

At block 1134, the system determines an emergency event score. In certain arrangements, the emergency event score is a sum of a highly abnormal event score and an abnormality score added to the summation of the products of abnormal events times the negative log-probabilities of the events.

The confirmation procedure determines at block 1136 whether any voice sounds are detectable and at block 1138 whether any motion of the user is detectable. If both voice activity and motion activity are detected, and if at block 1140 the emergency event score is less than an emergency event threshold, the system at block 1146 discards the emergency event score and at block 1148 flags the event as a 'False Positive'.

At block 1142, the system responds to a failure to detect either voice activity or motion activity or to an emergency event score greater than the emergency event threshold. Any one of these invokes action by the system whereby the system pushes a query to the user. Accordingly, the system attempts to determine the user's responsiveness. To determine the user's responsiveness, in certain arrangements, the system pushes a query to the user at block 1144. The query asks the user whether the user needs assistance. If the user responds 'No', then at block 1146 the system discards the emergency event score and at block 1148 flags the event as a 'False Positive'. However, if the user responds 'Yes' or fails to respond after a predetermined number of query attempts (e.g., two) by the system, then the system initiates a remedial response.

In certain arrangements, the system responds at block 1150 by identifying one or more potential responders. In some arrangements, the system identifies based on a geolocation determination an emergency responder located nearest to the user's current location. Optionally, the system can also search a list of emergency contacts prespecified by the user to initiate contact with one or more of the listed contacts. At block 1152, the system notifies one or more of the potential responders and notifies each of an emergency event affecting the user.

Figure 12:
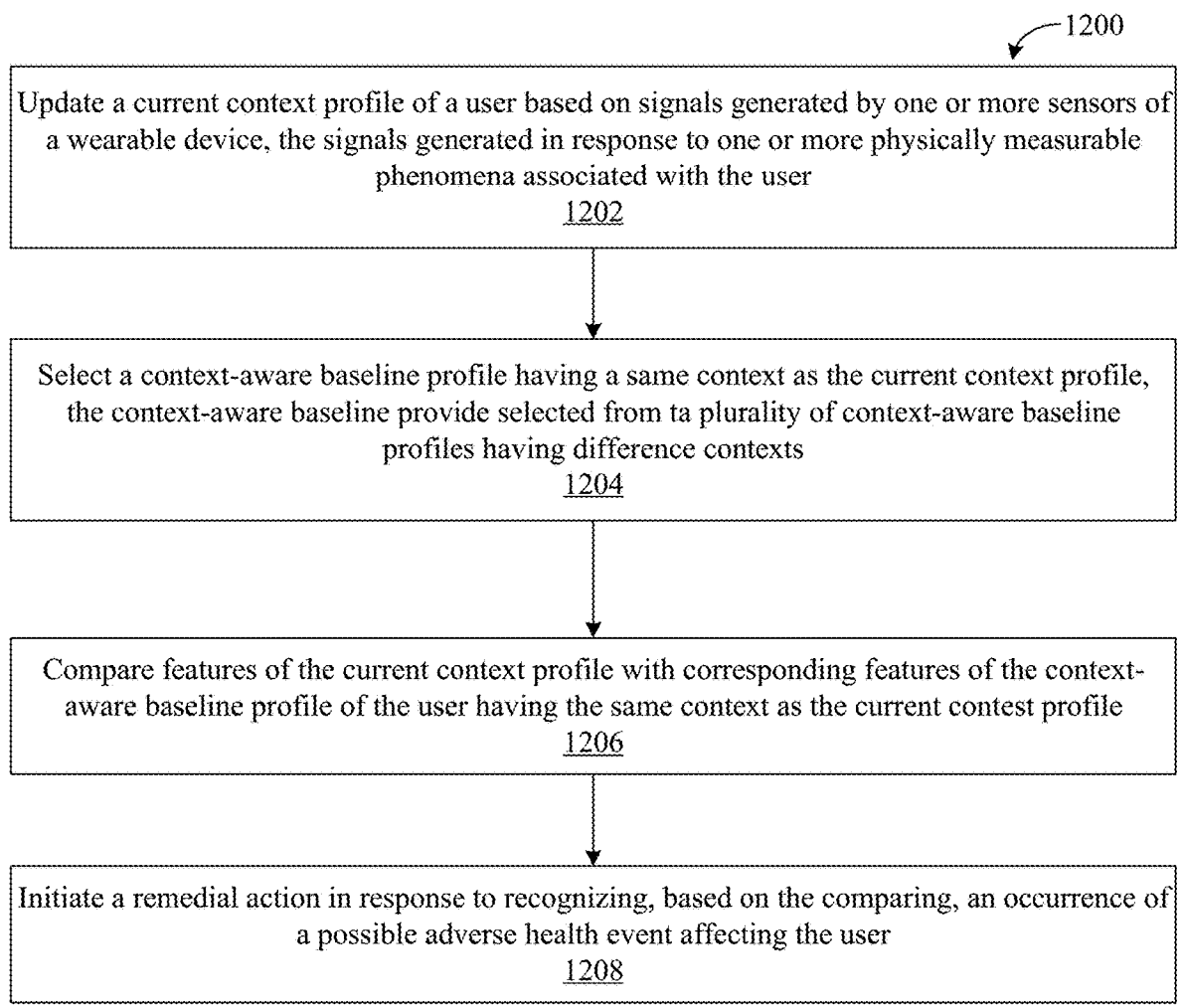
FIG. 12 illustrates an example method of adverse health event detection and emergency response.

FIG. 12 illustrates example method 1200 of adverse health detection and emergency response. Method 1200 can be performed by a device (or device operatively coupled to a companion device) including an adverse health detection and emergency response system as described herein (collectively "the system").

At block 1202, the system updates a current context profile of a user based on signals generated by one or more sensors of a device (e.g., wearable device), the signals generated in response to one or more physically measurable phenomena associated with the user. The system, at block 1204, selects a context-aware baseline profile having a same context as the current context profile. The context-aware baseline profile is selected from a plurality of context-aware baseline profiles having different contexts.

At block 1206, the system compares features of the current context profile with corresponding features of the context-aware baseline profile of the user having the same context as the current context profile. At block 1208, the system initiates a remedial action in response to recognizing, based on the comparing, an occurrence of a possible adverse health event affecting the user.

FIG. 13 illustrates an example device 1300 configured for operation as a system. Device 1300 (e.g., a wearable device or device and companion device operatively coupled thereto) can implement an adverse health event detection and emergency response system such as system 100. Device 1300 illustratively includes one or more processors 1302 coupled to memory 1304 through interface circuitry 1306. Device 1300 stores computer readable instructions (also referred to as "program code") within memory 1304, which is an example of computer readable storage media. Processor(s) 1302 execute the program code accessed from memory 1304 via interface circuitry 1306.

Memory 1304 can include one or more physical memory devices such as local memory 1308 and bulk storage device 1310, for example. Local memory 1308 is implemented as one or more non-persistent memory device(s) generally used during actual execution of the program code. Local memory 1308 is an example of a runtime memory. Examples of local memory 1308 include any of the various types of RAM suitable for use by a processor for executing program code. Bulk storage device 1310 is implemented as a persistent data storage device. Examples of bulk storage device 1310 include a hard disk drive (HDD), a solid-state drive (SSD), flash memory, a read-only memory (ROM), an erasable programmable read-only memory (EPROM), electrically erasable programmable read-only memory (EEPROM), or other suitable memory. Device 1300 can also include one or more cache memories (not shown) that provide temporary storage of at least some program code in order to reduce the number of times program code must be retrieved from a bulk storage device during execution.

Examples of interface circuitry 1306 include, but are not limited to, an input/output (I/O) subsystem, an I/O interface, a bus system, and a memory interface. For example, interface circuitry 1306 can be implemented as any of a variety of bus structures and/or combinations of bus structures including a memory bus or memory controller, a peripheral bus, an accelerated graphics port, and a processor or local bus.

In one or more example implementations, processor(s) 1302, memory 1304, and/or interface circuitry 1306 are implemented as separate components. Processor(s) 1302, memory 1304, and/or interface circuitry 1306 may be integrated in one or more integrated circuits. The various components in device 1300, for example, can be coupled by one or more communication buses or signal lines (e.g., interconnects and/or wires). Memory 1304 may be coupled to interface circuitry 1306 via a memory interface, such as a memory controller or other memory interface (not shown).

Device 1300 can include one or more displays. Illustratively, for example, device 1300 includes display 1312 (e.g., a screen). Display 1312 can be implemented as a touch-sensitive or touchscreen display capable of receiving touch input from a user. A touch sensitive display and/or a touch-sensitive pad is capable of detecting contact, movement, gestures, and breaks in contact using any of a variety of avail, able touch sensitivity technologies. Example touch sensitive technologies include, but are not limited to, capacitive, resistive, infrared, and surface acoustic wave technologies, and other proximity sensor arrays or other elements for determining one or more points of contact with a touch sensitive display and/or device.

Device 1300 can include multimedia sensors such as camera subsystem 1314. Camera subsystem 1314 can be coupled to interface circuitry 1306 directly or through a suitable input/output (I/O) controller. Camera subsystem 1314 can be coupled to optical sensor 1316. Optical sensor 1316 can be implemented using any of a variety of technologies. Examples of optical sensor 1316 can include, but are not limited to, a charged coupled device (CCD) or a complementary metal-oxide semiconductor (CMOS) optical sensor. Optical sensor 1316, for example, can be a depth sensor. Camera subsystem 1314 and optical sensor 1316 are capable of performing camera functions such as recording or capturing images and/or recording video.

Device 1300 can include other multimedia sensors such as an audio subsystem 1318. Audio subsystem 1318 can be coupled to interface circuitry 1306 directly or through a suitable input/output (I/O) controller. Audio subsystem 1318 can be coupled to a speaker 1320 and a microphone 1322 to facilitate voice-enabled functions, such as voice recognition, voice replication, digital recording, and telephony functions.

Device 1300 can include one or more wireless communication subsystems 1324. Each of wireless communication subsystem(s) 1324 can be coupled to interface circuitry 1306 directly or through a suitable I/O controller (not shown). Each of wireless communication subsystem(s) 1324 is capable of facilitating communication functions. Examples of wireless communication subsystems 1324 can include, but are not limited to, radio frequency receivers and transmitters, and optical (e.g., infrared) receivers and transmitters. The specific design and implementation of wireless communication subsystem 1324 can depend on the particular type of device 1300 implemented and/or the communication network(s) over which device 1300 is intended to operate.

As an illustrative and non-limiting example, wireless communication subsystem(s) 1324 may be designed to operate over one or more mobile networks, WiFi networks, short range wireless networks (e.g., a Bluetooth), and/or any combination of the foregoing. Wireless communication subsystem(s) 1324 can implement hosting protocols such that device 1300 can be configured as a base station for other wireless devices.

Device 1300 may include one or more sensors 1326, each of which can be coupled to interface circuitry 1306 directly or through a suitable I/O controller (not shown). Sensor(s) 1326 can include sensors for measuring the physiological condition or state of a user, such as an RIP sensor, pulse oximeter, EDA/GSR sensors, PPG sensor, and core body thermometer. Sensor(s) 1326 also can include movement-detecting sensors including one or more MEMS sensors. The MEMS sensor(s) can include, in different arrangements, accelerometers, magnetometers, and the like. In certain arrangements, MEMS sensor(s) can include one or more IMU that combine a MEMS accelerometer and a MEMS gyroscope. Other examples of sensors 1326 can include, but are not limited to, a location sensor (e.g., a GPS receiver and/or processor) capable of providing geo-positioning sensor data, an electronic magnetometer (e.g., an integrated circuit chip) capable of providing sensor data that can be used to determine the direction of magnetic North for purposes of directional navigation, an accelerometer capable of providing data indicating change of speed and direction of movement of device 1300 and an altimeter (e.g., an integrated circuit) capable of providing data indicating altitude. Sensor(s) 1326 can include Device 1300 further may include one or more input/output (I/O) devices 1328 coupled to interface circuitry 1306. I/O device(s) 1328 can be coupled to interface circuitry 1306 either directly or through intervening I/O controllers (not shown). Examples of I/O devices 1328 include, but are not limited to, a track pad, a keyboard, a display device, a pointing device, one or more communication ports (e.g., Universal Serial Bus (USB) ports), a network adapter, and buttons or other physical controls. A network adapter refers to circuitry that enables device 1300 to become coupled to other systems, computer systems, remote printers, and/or remote storage devices through intervening private or public networks. Modems, cable modems, Ethernet interfaces, and wireless transceivers not part of wireless communication subsystem(s) 1324 are examples of different types of network adapters that may be used with device 1300. One or more of I/O devices 1328 may be adapted to control functions of one or more or all of sensors 1326 and/or one or more of wireless communication subsystem(s) 1324.

Memory 1304 stores program code. Examples of program code include, but are not limited to, routines, programs, objects, components, logic, and other data structures. For purposes of illustration, memory 1304 stores an operating system 1330 and application(s) 1332. In addition, memory 1304 can an adverse health event detection and emergency response (AHEDER) system program code 1334 for implementing an AHEDER system, such as system 100 (FIG. 1).

Device 1300 is provided for purposes of illustration and not limitation. A device and/or system configured to perform the operations described herein can have a different architecture than illustrated in FIG. 13. The architecture can be a simplified version of the architecture described in connection with FIG. 13 that includes a memory capable of storing instructions and a processor capable of executing instructions. In this regard, device 1300 may include fewer components than shown or additional components not illustrated in FIG. 13 depending upon the particular type of device that is implemented. In addition, the particular operating system and/or application(s) included can vary according to device type as can the types of I/O devices included. Further, one or more of the illustrative components can be incorporated into, or otherwise form a portion of, another component. For example, a processor may include at least some memory.

Device 1300 can be implemented as a data processing system, a communication device, or other suitable system that is suitable for storing and/or executing program code. Device 1300 can be implemented as an edge device. Example implementations of device 1300 can include, but are not to limited to, earbuds, a smartwatch, a pair of smart glasses, an HMD device, or other wearable device, a smartphone or other portable device, laptop, tablet, or other computing device.

The terminology used herein is for the purpose of describing particular embodiments only and is not intended to be limiting. Notwithstanding, several definitions that apply throughout this document are expressly defined as follows.

As defined herein, the singular forms "a," "an," and "the" are intended to include the plural forms as well, unless the context clearly indicates otherwise.

The term "approximately" means nearly correct or exact, close in value or amount but not precise. For example, the term "approximately" may mean that the recited characteristic, parameter, or value is within a predetermined amount of the exact characteristic, parameter, or value.

As defined herein, the terms "at least one," "one or more," and "and/or," are open-ended expressions that are both conjunctive and disjunctive in operation unless explicitly stated otherwise. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B and C together.

As defined herein, the term "automatically" means without human intervention.

As defined herein, the term "computer readable storage medium" means a storage medium that contains or stores program code for use by or in connection with an instruction execution system, apparatus, or device. As defined herein, a "computer readable storage medium" is not a transitory, propagating signal per se. A computer readable storage medium may be, but is not limited to, an electronic storage device, a magnetic storage device, an optical storage device, an electromagnetic storage device, a semiconductor storage device, or any suitable combination of the foregoing. The different types of memory, as described herein, are examples of a computer readable storage media. A non-exhaustive list of more specific examples of a computer readable storage medium may include: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, or the like.

As defined herein, "data processing system" means one or more hardware systems configured to process data, each hardware system including at least one processor programmed to initiate operations and memory.

As defined herein, "execute" and "run" comprise a series of actions or events performed by the processor in accordance with one or more machine-readable instructions. "Running" and "executing," as defined herein refer to the active performing of actions or events by the processor. The terms run, running, execute, and executing are used synonymously herein.

As defined herein, the term "if" means "when" or "upon" or "in response to" or "responsive to," depending upon the context. Thus, the phrase "if it is determined" or "if [a stated condition or event] is detected" may be construed to mean "upon determining" or "in response to determining" or "upon detecting [the stated condition or event]" or "in response to detecting [the stated condition or event]" or "responsive to detecting [the stated condition or event]" depending on the context.

As defined herein, the terms "individual," "person," and "user" refer to a human being.

As defined herein, the term "processor" means at least one hardware circuit. The hardware circuit may be configured to carry out instructions contained in program code. The hardware circuit may be an integrated circuit. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "responsive to" and similar language as described above, (e.g., "if," "when," or "upon,") mean responding or reacting readily to an action or event. The response or reaction is performed automatically. Thus, if a second action is performed "responsive to" a first action, there is a causal relationship between an occurrence of the first action and an occurrence of the second action. The term "responsive to" indicates the causal relationship.

As defined herein, "real-time" means a level of processing responsiveness that a user or system senses as sufficiently immediate for a particular process or determination to be made, or that enables the processor to keep up with some external process. Relatedly, "real-time processing" means processing activity carried out in real-time.

As defined herein, "server" means a data processing system configured to share services with one or more other data processing systems. Relatedly, "client device" means a data processing system that requests shared services from a server, and with which a user directly interacts. Examples of a client device include, but are not limited to, a workstation, a desktop computer, a computer terminal, a mobile computer, a laptop computer, a netbook computer, a tablet computer, a smart phone, a personal digital assistant, a smart watch, smart glasses, a gaming device, a set-top box, a smart television, and the like. In one or more embodiments, the various user devices described herein may be client devices. Network infrastructure, such as routers, firewalls, switches, access points and the like, are not client devices as the term "client device" is defined herein.

As defined herein, "substantially" means that the recited characteristic, parameter, or value need not be achieved exactly, but that deviations or variations, including for example, tolerances, measurement error, measurement accuracy limitations, and other factors known to those of skill in the art, may occur in amounts that do not preclude the effect the characteristic was intended to provide.

The terms first, second, etc. may be used herein to describe various elements. These elements should not be limited by these terms, as these terms are only used to distinguish one element from another unless stated otherwise or the context clearly indicates otherwise.

A computer program product may include a computer readable storage medium (or media) having computer readable program instructions thereon for causing a processor to carry out aspects of the present invention. Within this disclosure, the term "program code" is used interchangeably with the term "computer readable program instructions." Computer readable program instructions described herein may be downloaded to respective computing/processing devices from a computer readable storage medium or to an external computer or external storage device via a network, for example, the Internet, a LAN, a WAN and/or a wireless network. The network may include copper transmission cables, optical transmission fibers, wireless transmission, routers, firewalls, switches, gateway computers and/or edge devices including edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations for the inventive arrangements described herein may be assembler instructions, instruction-set-architecture (ISA) instructions, machine instructions, machine dependent instructions, microcode, firmware instructions, or either source code or object code written in any combination of one or more programming languages, including an object-oriented programming language and/or procedural programming languages. Computer readable program instructions may specify state-setting data. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some cases, electronic circuitry including, for example, programmable logic circuitry, an FPGA, or a PLA may execute the computer readable program instructions by utilizing state information of the computer readable program instructions to personalize the electronic circuitry, in order to perform aspects of the inventive arrangements described herein.

Certain aspects of the inventive arrangements are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, may be implemented by computer readable program instructions, e.g., program code.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. In this way, operatively coupling the processor to program code instructions transforms the machine of the processor into a special-purpose machine for carrying out the instructions of the program code. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the operations specified in the flowchart and/or block diagram block or blocks.

The computer readable program instructions may also be loaded onto a computer, other programmable data processing apparatus, or other device to cause a series of operations to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various aspects of the inventive arrangements. In this regard, each block in the flowcharts or block diagrams may represent a module, segment, or portion of instructions, which comprises one or more executable instructions for implementing the specified operations. In some alternative implementations, the operations noted in the blocks may occur out of the order noted in the figures. For example, two blocks shown in succession may be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts or carry out combinations of special purpose hardware and computer instructions.

The corresponding structures, materials, acts, and equivalents of all means or step plus function elements that may be found in the claims below are intended to include any structure, material, or act for performing the function in combination with other claimed elements as specifically claimed.

The description of the embodiments provided herein is for purposes of illustration and is not intended to be exhaustive or limited to the form and examples disclosed. The terminology used herein was chosen to explain the principles of the inventive arrangements, the practical application or technical improvement over technologies found in the marketplace, and/or to enable others of ordinary skill in the art to understand the embodiments disclosed herein. Modifications and variations may be apparent to those of ordinary skill in the art without departing from the scope and spirit of the described inventive arrangements. Accordingly, reference should be made to the following claims, rather than to the foregoing disclosure, as indicating the scope of such features and implementations.

What is claimed is:

1. A method comprising:
   updating a current context profile of a user based on signals generated by one or more sensors of a wearable device, the signals generated in response to one or more physically measurable phenomena associated with the user;
   selecting a context-aware baseline profile having a same context as the current context profile, the context-aware baseline profile selected from a plurality of context-aware baseline profiles having different contexts;
   comparing features of the current context profile with corresponding features of the context-aware baseline profile of the user having the same context as the current context profile;
   initiating a remedial action in response to recognizing, based on the comparing, an occurrence of a possible adverse health event affecting the user; and
   intermittently updating the current context profile, wherein a frequency of the updating is determined based on identifying a risk category of the user based on user demographic data.

2. The method of claim 1, wherein
   the features of the current context profile and the context-aware baseline profile include one or more of physiological data, activity data, and environmental data corresponding to the user.

3. The method of claim 1, further comprising:
   adjusting a frequency of intermittently updating the current context profile in response to a deviation between one or more corresponding features of the current context profile and the context-aware baseline profile.

4. The method of claim 1, wherein
   one or more the plurality of context-aware baseline profiles is generated, at least in part, based on data corresponding to other users identified as demographically similar to the user.

5. The method of claim 1, wherein the remedial action comprises:
   determining a responsiveness of the user; and
   in response to an acknowledged request from the user or in response to determining that the user is unresponsive, conveying one or more emergency notifications to at least one of an emergency responder or other entity.

6. The method of claim 5, wherein
   the other entity is a pre-specified contact of the user, the method comprising:
   determining a location of the pre-specified contact of the user;
   determining a distance from the user to the pre-specified contact of the user; and
   in response to determining that the distance is within a predetermined distance threshold, providing the notification to the pre-specified user.

7. The method of claim 1, wherein the remedial action comprises:
   generating an adverse health event score based on a sum of weighted deviations between elements of the current context profile and corresponding elements of the corresponding context-aware baseline profile; and
   activating an event confirmation procedure in response to the adverse health event score exceeding a predetermined threshold.

8. The method of claim 7, wherein the event confirmation procedure comprises:
   activating at least one multimedia sensor;
   classifying at least one multimedia event captured by the at least one multimedia sensor;
   generating an emergency event score based, at least in part, on the classifying the at least one multimedia event;
   responsive to the emergency event score exceeding a predetermined threshold, determining a responsiveness of the user; and
   conveying one or more emergency notifications in response to an acknowledged request from the user or in response to determining that the user is unresponsive.

9. A system, comprising:
   a plurality of sensors; and
   one or more processors operatively coupled with the plurality of sensors, the one or more processors configured to initiate operations including:
      updating a current context profile of a user based on signals generated by one or more sensors of the plurality of sensors, the signals generated in response to one or more physically measurable phenomena associated with the user;
      selecting a context-aware baseline profile having a same context as the current context profile, the context-aware baseline profile selected from a plurality of context-aware baseline profiles having different contexts;
      comparing features of the current context profile with corresponding features of the context-aware baseline profile of the user having the same context as the current context profile;
      initiating a remedial action in response to recognizing, based on the comparing, an occurrence of a possible adverse health event affecting the user; and adjusting a frequency of intermittently updating the current context profile in response to a deviation between one or more corresponding features of the current context profile and the context-aware baseline profile.

10. The system of claim 9, wherein
the features of the current context profile and the context-aware baseline profile include one or more of physiological data, activity data, and environmental data corresponding to the user.

11. The system of claim 9, wherein the processor is configured to initiate operations further including:
intermittently updating the current context profile, wherein a frequency of the updating is determined based on identifying a risk category of the user based on user demographic data.

12. The system of claim 9, wherein
one or more of the plurality of context-aware baseline profiles is generated, at least in part, based on data corresponding to other users identified as demographically similar to the user.

13. The system of claim 9, wherein the remedial action comprises:
determining a responsiveness of the user; and
in response to an acknowledged request from the user or in response to determining that the user is unresponsive, conveying one or more emergency notifications to at least one of an emergency responder or other entity.

14. The system of claim 13, wherein
the other entity is a pre-specified contact of the user, the operations comprising:
determining a location of the pre-specified contact of the user;
determining a distance from the user to the pre-specified contact of the user; and
in response to determining that the distance is within a predetermined distance threshold, providing the notification to the pre-specified user.

15. The system of claim 9, wherein the remedial action comprises:
generating an adverse health event score based on a sum of weighted deviations between elements of the current context profile and corresponding elements of the corresponding context-aware baseline profile; and
activating an event confirmation procedure in response to the adverse health event score exceeding a predetermined threshold.

16. The system of claim 15, wherein the event confirmation procedure comprises:

activating at least one multimedia sensor;
classifying at least one multimedia event captured by the at least one multimedia sensor;
generating an emergency event score based, at least in part, on the classifying the at least one multimedia event;
responsive to the emergency event score exceeding a predetermined threshold, determining a responsiveness of the user; and
conveying one or more emergency notifications in response to an acknowledged request from the user or in response to determining that the user is unresponsive.

17. A computer program product, the computer program product comprising:
one or more computer-readable storage media and program instructions collectively stored on the one or more computer-readable storage media, the program instructions executable by a processor to cause the processor to initiate operations including:
updating a current context profile of a user based on signals generated by one or more sensors of a plurality of sensors, the signals generated in response to one or more physically measurable phenomena associated with the user;
selecting a context-aware baseline profile having a same context as the current context profile, the context-aware baseline profile selected from a plurality of context-aware baseline profiles having different contexts;
comparing features of the current context profile with corresponding features of the context-aware baseline profile of the user having the same context as the current context profile;
initiating a remedial action in response to recognizing, based on the comparing, an occurrence of a possible adverse health event affecting the user;
generating an adverse health event score based on a sum of weighted deviations between elements of the current context profile and corresponding elements of the corresponding context-aware baseline profile; and
activating an event confirmation procedure in response to the adverse health event score exceeding a predetermined threshold.

18. The computer program product of claim 17, wherein
the features of the current context profile and the context-aware baseline profile include one or more of physiological data, activity data, and environmental data corresponding to the user.

* * * * *